United States Patent
Hoffmann et al.

(10) Patent No.: US 12,287,337 B2
(45) Date of Patent: *Apr. 29, 2025

(54) AUTOANTIBODY BIOMARKERS OF OVARIAN CANCER

(71) Applicant: ADELAIDE RESEARCH & INNOVATION PTY LTD, Adelaide (AU)

(72) Inventors: Peter Hoffmann, Largs North (AU); Martin Oehler, St. Georges (AU); Karina Martin, Largs North (AU)

(73) Assignee: ADELAIDE RESEARCH & INNOVATION PTY LTD, Adelaide (AU)

( * ) Notice: Subject to any disclaimer, the term of this patent is extended or adjusted under 35 U.S.C. 154(b) by 379 days.

This patent is subject to a terminal disclaimer.

(21) Appl. No.: 17/826,948

(22) Filed: May 27, 2022

(65) Prior Publication Data

US 2022/0365088 A1 Nov. 17, 2022

Related U.S. Application Data

(60) Division of application No. 16/245,822, filed on Jan. 11, 2019, now Pat. No. 11,371,993, which is a continuation of application No. 15/023,155, filed as application No. PCT/AU2014/000925 on Sep. 18, 2014, now abandoned.

(30) Foreign Application Priority Data

Sep. 18, 2013 (AU) .............................. 2013903595

(51) Int. Cl.
*G01N 33/574* (2006.01)
*C07K 16/30* (2006.01)
*G01N 33/564* (2006.01)
*G01N 33/68* (2006.01)

(52) U.S. Cl.
CPC ... *G01N 33/57449* (2013.01); *C07K 16/3069* (2013.01); *G01N 33/564* (2013.01); *G01N 33/6854* (2013.01); *G01N 2500/00* (2013.01)

(58) Field of Classification Search
CPC ................................................ C07K 16/3069
See application file for complete search history.

(56) References Cited

U.S. PATENT DOCUMENTS

| | | |
|---|---|---|
| 2002/0168696 A1 | 11/2002 | Hanash et al. |
| 2008/0300141 A1 | 12/2008 | Tainsky et al. |
| 2012/0003225 A1 | 1/2012 | Patz, Jr. et al. |
| 2012/0277326 A1 | 11/2012 | Taylor et al. |
| 2014/0179808 A1 | 6/2014 | Flanagan |
| 2015/0362497 A1 | 12/2015 | Anderson et al. |

FOREIGN PATENT DOCUMENTS

| | | |
|---|---|---|
| JP | 2008-309612 | 12/2008 |
| JP | 2010-503845 | 2/2010 |
| JP | 2012-198231 | 10/2012 |
| WO | WO 00/54805 | 9/2000 |
| WO | WO 01/74858 | 10/2001 |
| WO | WO 2008/032084 | 3/2008 |
| WO | WO 2008/115710 | 9/2008 |
| WO | WO 2009/064657 | 5/2009 |
| WO | WO 2010/070043 | 6/2010 |
| WO | WO 2013/112801 | 8/2013 |

OTHER PUBLICATIONS

Albarracin et al., "Prognostic Significance and Histotype-Specific Expression of Annexia I in Human Ovarian Cancers," *Lab Invest.*, vol. 83:178A MA 813, 2003.
An et al., "Comparative Proteomics of Ovarian Epithelial Tumors," *J. Proteome Res.*, vol. 5:1082-1090, 2006.
Buford et al., "Autoantibodies to MUC1 Glycopeptides Cannot be used as a Screening Assay for Early Detection of Breast, Ovarian, Lung or Pancreatic Cancer," *Br. J. Cancer*, vol. 108:2045-2055, 2013.
Chapman et al., "Immunobiomarkers in Small Cell Lung Cancer: Potential Early Cancer Signals," *Clin. Cancer Res.*, vol. 17:1474-1480, 2011.
Charoentong et al., "Pan-cancer Immunogenomic Analyses Reveal Genotype-Immunophenotype Relationships and Predictors of Response to Checkpoint Blockade," *Cell Reports* 18:248-262, 2017.
Gharesi-Fard et al., "Presence of Auto-Antibody Against Two Placental Proteins, Annexin A1 and Vitamin D Binding Protein, in Sera of Women with Pre-eclampsia," *J. Reprod. Immunol.* (Abstract P114) vol. 94:94, 2012.
Gharesi-Fard et al., "Presence of Auto-Antibody Against Two Placental Proteins, Annexin A1 and Vitamin D Binding Protein, in Sera of Women with Pre-eclampsia," *J. Reprod. Immunol.*, vol. 99:10-16, 2013.
Hwee et al., "Serum antibodies as biomarkers for early cancer detection," *FEBS J* 276:6880-6904, 2009.
Martin et al., "Exploring the Immunoproteome for Ovarian Cancer Biomarker Discovery," *Int. J. Mol. Sci.*, vol. 12:410-428, 2011.
Murphy et al., "Assessment of the humoral immune response to cancer," *J Proteomics* 75:4573-4579, 2012.

(Continued)

*Primary Examiner* — Mark Halvorson
(74) *Attorney, Agent, or Firm* — Klarquist Sparkman, LLP

(57) ABSTRACT

The present invention relates to the identification of biological markers of ovarian cancer. Specifically, cancer-associated autoantibodies to ANXA1, ARP3, SAHH, SERPH, ARAP1, OTUB1, ATP1A1, UBA1, and CFAH have been identified in subjects with early stage ovarian cancer. These autoantibodies can be utilised for a range of purposes including methods for detecting ovarian cancer, methods for screening for early stage ovarian cancer, and methods for assessing treatment response as well as disease progression and recurrence. The autoantibodies also represent prognostic markers of ovarian cancer development.

20 Claims, 14 Drawing Sheets

(56) References Cited

OTHER PUBLICATIONS

Murray et al., "Technical Validation of an Autoantibody Test for Lung Cancer," *Ann. Oncol.*, vol. 21:1687-1693, 2010.
Supplementary European Search Report dated Mar. 24, 2017 from European Application No. 14846089 (2 pages).
Tan et al., "Serum Autoantibodies as Biomarkers for Early Cancer Detection," *FEBS J.*, vol. 276:6880-6904, 2009.

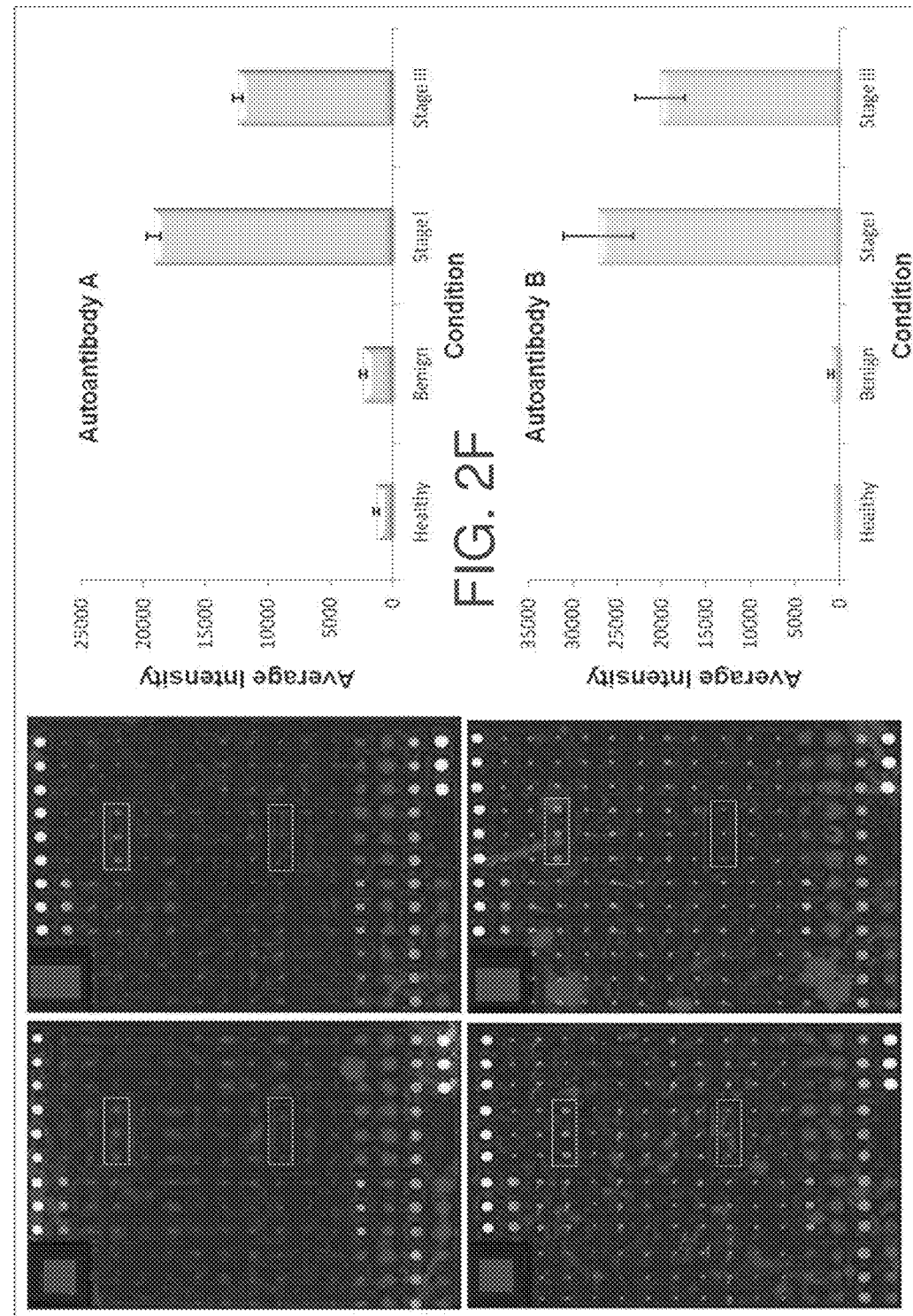

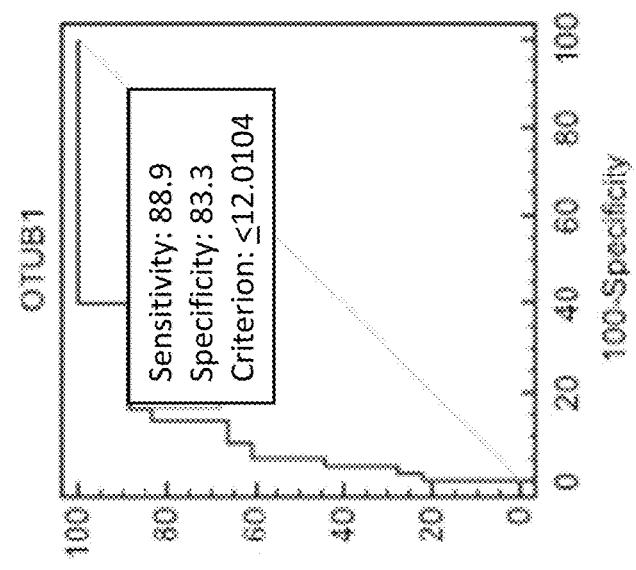
FIG. 5D  FIG. 5E  FIG. 5F
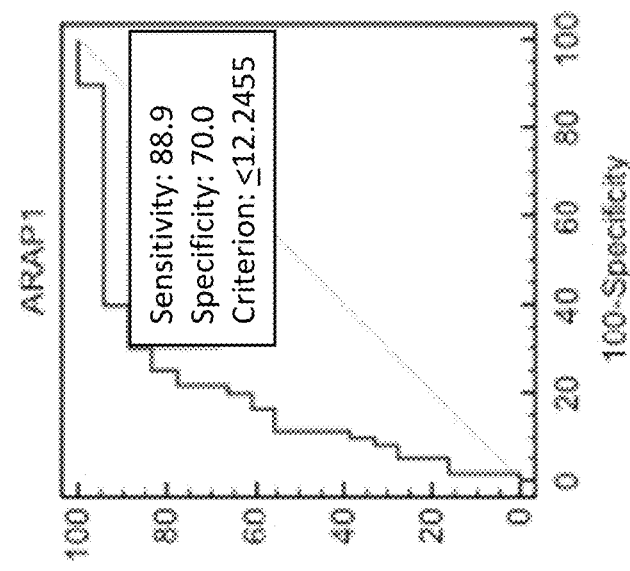
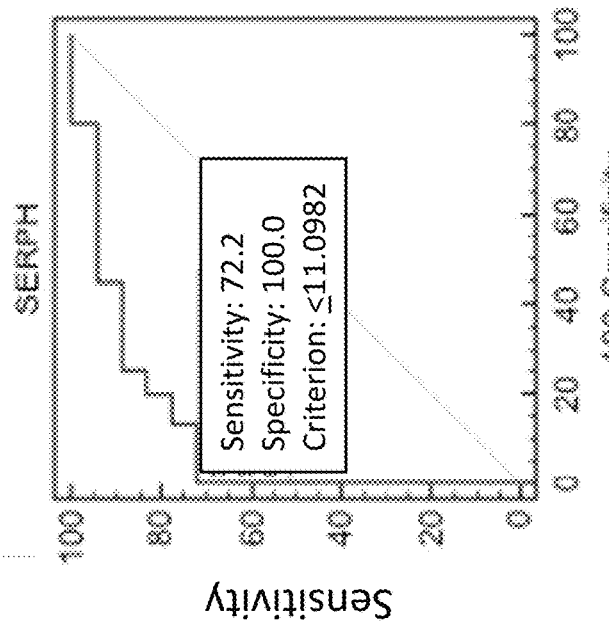

AUTOANTIBODY BIOMARKERS OF OVARIAN CANCER

PRIORITY CLAIM

This is a divisional of U.S. patent application Ser. No. 16/245,822, filed Jan. 11, 2019, issued as U.S. Pat. No. 11,371,993 on Jun. 28, 2022, which is a continuation of U.S. patent application Ser. No. 15/023,155, filed Mar. 18, 2016, which is the U.S. National Stage of International Application No. PCT/AU2014/000925, filed Sep. 18, 2014, which claims priority to Australian Provisional Application No. 2013903595, filed Sep. 18, 2013. The contents of the above-referenced applications are herein incorporated by reference.

FIELD OF THE INVENTION

The present invention relates to the identification of biological markers of ovarian cancer. Specifically, cancer-associated autoantibodies have been identified in subjects with early stage ovarian cancer. These autoantibodies can be utilised for a range of purposes including methods for detecting ovarian cancer, methods for screening for early stage ovarian cancer, and methods for assessing treatment response as well as disease progression and recurrence. The autoantibodies also represent prognostic markers of ovarian cancer development.

BACKGROUND OF THE INVENTION

Ovarian cancer is the leading cause of death from gynaecological malignancies and the fifth leading cause of all cancer-related deaths in women. Indeed, it has been estimated that in the United States one woman in 72 will develop ovarian cancer in her lifetime, and that one woman in 96 will die of the disease. For example, for 2013 it has been estimated that in the United States alone 22,240 new diagnoses of ovarian cancer will be made and 14,030 women will die from the disease.

The most widely recognised risk factors for ovarian cancer are menstrual, reproductive and hormonal factors. However, a number of other factors that have also been linked to the development of ovarian cancer and these include diet, adult height, weight and smoking. Furthermore, there have been clinical observations suggesting a genetic component to ovarian cancer risk due to familial aggregations of ovarian cancer. Indeed, women carrying BRCA1 and BRCA2 mutations have been seen to be at higher risk of developing ovarian cancer.

The high mortality rate of ovarian cancer arises due to the asymptomatic progression of the disease resulting in 60% of cases being diagnosed in advanced stages (International Federation of Gynecology and Obstetrics (FIGO) stage III and IV) when the cancer has spread to the abdominal cavity or to other organs. Detection of ovarian cancer when it is still confined to the ovary (FIGO stage I) is associated with a 5-year survival rate of about 90% compared to less than 30% for women presenting with advanced ovarian disease (FIGO stage III/IV). Therefore, the detection of ovarian cancer at an early stage is the best way to improve overall survival from the disease. However, at present there are no clinically applicable tests and biological markers available for the early detection and screening of ovarian cancer.

To date, cancer antigen 125 (CA125) and HE4 are the only two protein-based biomarkers that have been clinically approved to distinguish benign from malignant ovarian lesions, to measure disease burden, and to evaluate ovarian cancer treatment. However, these markers are not elevated in all patients with ovarian cancer and may be increased in healthy women or women with benign diseases. Consequently, they do not have sufficient sensitivity and specificity for population-based risk assessment or early detection. For example, serum levels of CA125 greater than 35 U/mL in women presenting with an adnexal mass is the current gold standard for detection. However, elevated levels of CA125 are only observed in 50% of early stage patients and 80% of advanced stage patients.

There are several profound obstacles associated with traditional biomarker discovery focused on tumour-associated antigens. For example, there are quantitative obstacles in early-stage disease when the tumour is very small and therefore only very small quantities of the target antigen are produced (which might remain undetectable with currently available technology). There are also qualitative issues as the markers in many cases are incidental to the disease process and are often masked by the complexity of the examined biospecimens. The problem is further compounded by the genetic diversity of human populations and the influence of uncontrollable environmental factors meaning that potential biomarkers can be overshadowed by the high degree of natural variation in biomarker expression. Finally, obtaining a significant number of human samples of early-stage ovarian cancer for research is difficult due to the rarity of the disease at this stage.

Given the lack of early detection tests and limitations of current approaches, there is an urgent need to identify new biomarkers for early ovarian cancer.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The inventors have recognised that autologous antibodies against tumour-associated antigens may serve as sensitive markers for ovarian cancer detection. Circulating autoantibodies against tumour-associated antigens are more abundant than antigens, especially with low tumour burden at early stage of the disease, and are also more stable than serum antigens. Furthermore, autoantibodies have been observed to appear before the manifestation of the malignancy. The inventors have now identified a number of autoantibodies that display high sensitivity and specificity for early ovarian cancer.

Accordingly, in a first aspect the present invention provides a method of detecting ovarian cancer in a subject, the method including the step of detecting the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

The inventors have established that the aforementioned ovarian cancer-associated autoantibodies are produced by patients with the earliest stages of ovarian cancer.

Accordingly, in a second aspect the present invention provides a method of screening for early stage ovarian cancer in a subject, the method including the step of testing for the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the early stage ovarian cancer is stage I carcinoma.

Identification of the aforementioned ovarian cancer-associated autoantibodies in patients with early stage ovarian cancer also enables methods for assessing the therapeutic efficacy in a subject of a treatment for the cancer.

Accordingly, in a third aspect the present invention provides a method of assessing progression or recurrence of ovarian cancer in a subject, the method including the step of detecting the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the method includes:

(a) detecting the level of the one or more ovarian cancer-associated autoantibodies in the subject;

(b) comparing the level of the one or more ovarian cancer-associated autoantibodies in the subject to a reference level for the or each ovarian cancer-associated autoantibody; and (c) assessing the progression or recurrence of ovarian cancer in the subject on the basis of the comparison.

In one embodiment, the subject is undergoing treatment for the ovarian cancer. In some embodiments, a level of the one or more ovarian cancer-associated autoantibodies in the subject that is higher than the reference level for the, or each, ovarian cancer-associated autoantibody is indicative of the progression or recurrence of ovarian cancer in the subject.

In some embodiments of the aforementioned aspects of the invention, the presence or level of the one or more ovarian cancer-associated autoantibodies is detected in a sample obtained from the subject. In some embodiments, the sample is selected from any one or more of the group consisting of serum, whole blood, blood plasma, saliva, buccal swab, cervical pap smears, stool, urine, bladder washing, uterine washing, sputum, lymphatic fluid, cerebrospinal fluid, semen, and a tissue sample from one or both ovaries or metastatic tumour tissue of the subject.

In some embodiments of the aforementioned aspects of the invention, the presence or level of the one or more ovarian cancer-associated autoantibodies in the subject is detected by an agent that binds to, or interacts with, the one or more ovarian cancer-associated autoantibodies. In one embodiment, the agent is an antigen from which the one or more ovarian cancer-associated autoantibodies was derived or is an antibody specific for the one or more ovarian cancer-associated autoantibodies. In one embodiment, the agent is detectably labelled.

In some embodiments of the aforementioned aspects of the invention, the presence or level of an autoantibody to ANXA1, an autoantibody to ARP3, and an autoantibody to SAHH is detected in the subject. In some embodiments, the presence or level of an autoantibody to ANXA1, an autoantibody to ARP3, an autoantibody to SAHH, and an autoantibody to SERPH is detected in the subject. In some embodiments, the presence or level of an autoantibody to ANXA1, an autoantibody to ARP3, an autoantibody to SAHH, and tumour associated antigen CA125 is detected in the subject.

In a fourth aspect the present invention provides a method of screening a candidate therapeutic agent useful for treating ovarian cancer in a subject, the method including the step of assaying the candidate therapeutic agent for activity in reducing a level of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the method includes:

(a) administering the candidate therapeutic agent to the subject;

(b) detecting the level of the one or more ovarian cancer-associated autoantibodies in the subject; and (c) comparing the level of the one or more ovarian cancer-associated autoantibodies in the subject to the level of the one or more ovarian cancer-associated autoantibodies in an untreated subject having ovarian cancer, wherein if the level of the one or more ovarian cancer-associated autoantibodies in the subject is lower than the level of the one or more ovarian cancer-associated autoantibodies in the untreated subject, the candidate therapeutic agent is useful for treating ovarian cancer.

In one embodiment, the level of the one or more ovarian cancer-associated autoantibodies is detected in a sample obtained from the subject. The sample may be selected from one or more of those listed above.

In some embodiments of the fourth aspect of the invention the level of the one or more ovarian cancer-associated autoantibodies in the subject is detected by an agent that binds to, or interacts with, the one or more ovarian cancer-associated autoantibodies. The agent may be selected from those listed above, and may be detectably labelled.

In some embodiments of the fourth aspect of the invention the level of an autoantibody to ANXA1, an autoantibody to ARP3, and an autoantibody to SAHH is detected in the subject. In some embodiments, the level of an autoantibody to ANXA1, an autoantibody to ARP3, an autoantibody to SAHH, and an autoantibody to SERPH is detected in the subject. In some embodiments, the level of an autoantibody to ANXA1, an autoantibody to ARP3, an autoantibody to SAHH, and tumour associated antigen CA125 is detected in the subject.

In a fifth aspect the present invention provides a composition for detecting ovarian cancer in a subject, for screening for early stage ovarian cancer in a subject and/or for assessing progression of ovarian cancer in a subject, the composition including an agent that binds to, or interacts with, one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the the agent is an antigen from which the one or more ovarian cancer-associated autoantibodies was derived or is an antibody specific for the one or more ovarian cancer-associated autoantibodies. In one embodiment, the agent is detectably labelled.

In some embodiments of the fifth aspect of the invention the one or more ovarian cancer-associated autoantibodies include an autoantibody to ANXA1, an autoantibody to ARP3, and an autoantibody to SAHH. In some embodiments, the one or more ovarian cancer-associated autoantibodies include an autoantibody to ANXA1, an autoantibody to ARP3, an autoantibody to SAHH, and an autoantibody to SERPH. In some embodiments of the fifth aspect of the invention, the composition further includes an agent that binds to, or interacts with, tumour associated antigen CA125.

In a sixth aspect the present invention provides a kit for detecting ovarian cancer in a subject, for screening for early stage ovarian cancer in a subject, and/or for assessing progression of ovarian cancer in a subject, the kit including means for detecting the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH. In one embodiment, the kit further includes means for detecting tumour associated antigen CA125 in the subject.

BRIEF DESCRIPTION OF THE FIGURES

For a further understanding of the aspects and advantages of the present invention, reference should be made to the following detailed description, taken in conjunction with the accompanying drawings.

FIGS. 2A-2F—Representative protein microarrays demonstrating differential regulation of two autoantibody candidates. (FIG. 2A) healthy, (FIG. 2B) benign, (FIG. 2C) stage I and (FIG. 2D) stage II serum. Autoantibody A signal (measured as average intensity) is shown in FIG. 2E, while autoantibody B signal is shown in FIG. 2F.

FIG. 3A shows the Antigen mean/SD for all samples. X-axis—Mean (Population); Y-axis— SD (Population). FIG. 3B: X-axis—Theoretical Quantiles; Y-axis—Sample Quantiles (Normalized Intensity). FIG. 3C: X-axis—Population Mean (vsn data); Y-axis—Population SD (vsn data). FIG. 3D: X-axis—Theoretical Quantiles; Y-axis—Sample Quantiles (Normalized Intensity vsn).

FIGS. 5A-5I— Receiver-operating characteristic (ROC) curves of the nine individual autoantibody biomarkers.

DETAILED DESCRIPTION OF THE INVENTION

Figure 1:
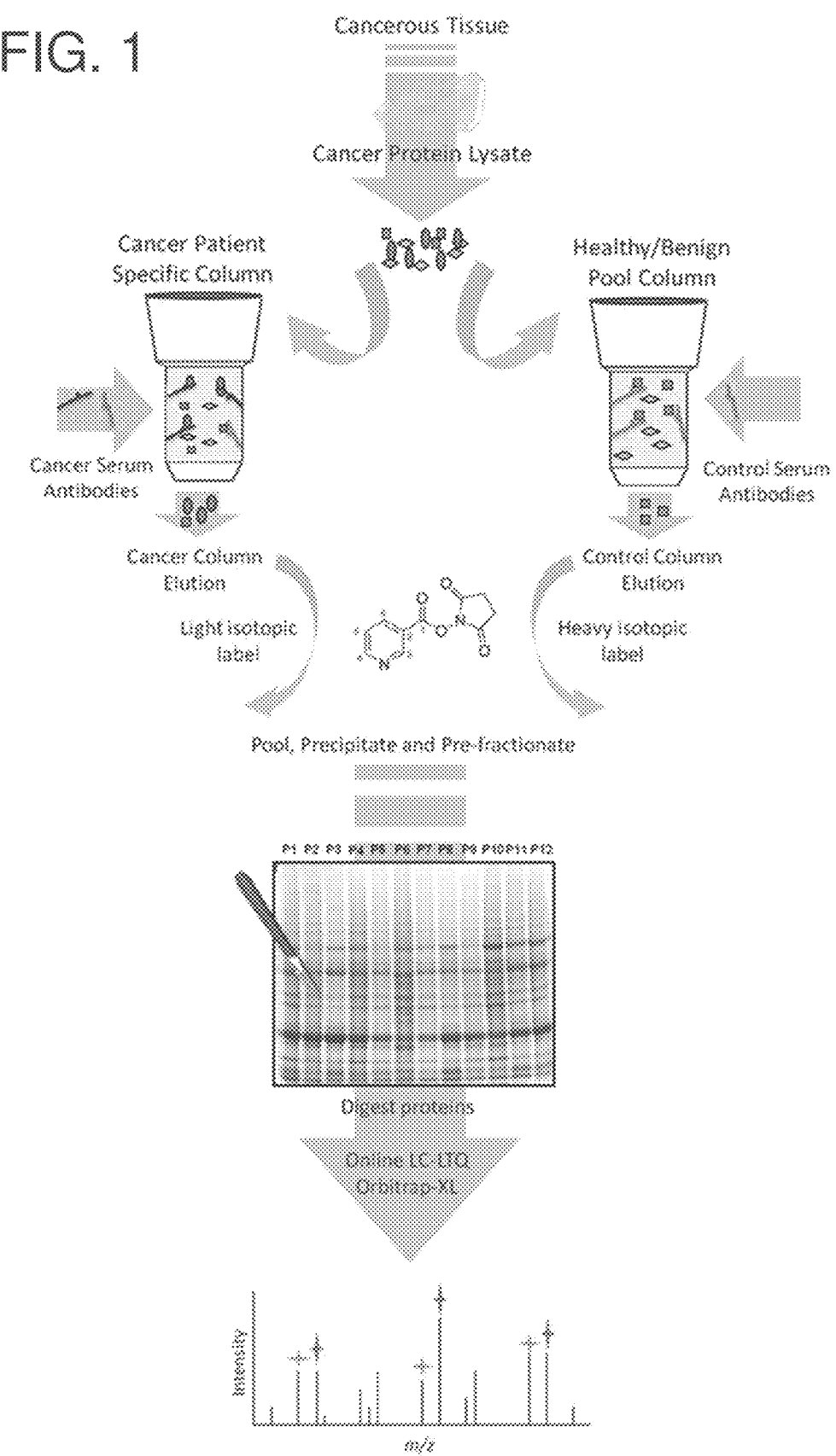
FIG. 1—A schematic describing the immunoproteomic approach used to identify the ovarian cancer autoantibodies of the present invention.

The present invention is predicated in part on the identification of a number of autoantibodies that are specific for antigens present on ovarian cancer cells. The high sensitivity and specificity of these antibodies for ovarian cancer indicates that they are suitable biomarkers which can form the basis of diagnostic and prognostic testing for ovarian cancer.

A biomarker is effectively an organic biomolecule which is differentially present in a sample taken from a subject of one phenotypic status (e.g. having a disease) as compared with another phenotypic status (e.g. not having the disease). A biomarker is differentially present between different phenotypic status groups if the mean or median level or amount of the biomarker is calculated to be different (e.g. present/absent, higher/lower) between the groups. Therefore, biomarkers, alone or in combination, provide an indication that a subject belongs to one phenotypic status or another. With respect to autoantibodies that are specific for a particular type of cancer, generally these would only be expected to be present in a subject having that cancer, but not present in a "normal" subject not having that cancer. However, it is to be made clear that the biomarkers of the present invention are detectable at the earliest stages of ovarian cancer development and therefore are likely to be present in affected subjects who considered themselves "normal" due to lack of phenotypic expression of the ovarian cancer.

Accordingly, in a first aspect the present invention provides a method of detecting ovarian cancer in a subject, the method including the step of detecting the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

Through testing for the presence of the aforementioned autoantibodies in subjects at various stages of serous ovarian cancer, the inventors have determined that each of these biomarkers is present at the early stages of ovarian disease (stage I and beyond).

Accordingly, in a second aspect the present invention provides a method of screening for early stage ovarian cancer in a subject, the method including the step of testing for the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the early stage ovarian cancer is stage I carcinoma. The stage of a cancer is determined by the extent of which the cancer has spread. Stage I ovarian cancer is defined by the cancerous cells being localised to the ovary with the cancerous cells yet to spread to the pelvic surfaces or organs (stage 2), abdominal cavity or lymph nodes (stage 3) and distant organs (stage 4). Accordingly, stage I ovarian cancer is localised to one or both ovaries.

The meaning of "ovarian cancer" would be well understood by a person skilled in the art. For the avoidance of doubt, an ovarian cancer is a cancerous growth arising from the ovary. More than 90% of ovarian cancers are epithelial in origin given that they originate from the surface of the ovary. However, it is believed that the fallopian tubes may also be the source of some ovarian cancers and so cancer developing from the fallopian tubes are also encompassed by the term "ovarian cancer". Ovarian cancers are also categorised as gynaecological cancers.

As indicated above, autoantibodies are antibodies that are produced by a subject in response to a protein (antigen) present in the subject. In general, individuals do not generate an immune response to their native proteins and therefore do not produce antibodies against them. However, in rare instances individuals do recognise their own native proteins as antigens and produce antibodies to them. This leads to various autoimmune diseases such as rheumatoid arthritis and systemic lupus erythematosus. With respect to the present invention, the autoantibodies of the present invention are not produced in response to the subject's own native proteins, but are produced in response to the presence of proteins in the subject that are specifically associated with cancerous cells present in the subject. These proteins are known as tumour-associated antigens.

Detecting the presence, or testing for the presence, of an autoantibody in a subject can be achieved a number of ways as would be understood by a person skilled in the art. In one embodiment, an agent that binds to, or interacts with, the one or more ovarian cancer-associated autoantibodies of the present invention may be used. The agent may bind to the autoantibody directly or may interact with the autoantibody in an indirect manner, for example by binding to one or more intermediary ligands that target the autoantibody. The agent may be any molecule, substance or reagent that specifically targets the autoantibody under investigation. Exemplary agents are described in further detail below.

In some embodiments, the agent may be the tumour associated protein (antigen) from which the autoantibody was derived. For example, the autoantibody to ANXA1 may be detected by use of the ANXA1 protein itself. However, any part or portion of the antigen that can specifically bind to the corresponding autoantibody is encompassed by the present invention. Therefore, an autoantibody may be detected through use of a fragment of the antigen provided it can be recognised by the autoantibody. In this regard, the fragment of the antigen may consist of as little as about 5 amino acid residues of the antigen; however, the fragment may consist of at least 5, at least 6, at least 7, at least 8, at least 9, at least 10, at least 15, at least 20, at least 25, at least 30, at least 35, at least 40, at least 45, at least 50, or more than 50 amino acid residues of the antigen. Preferably, the fragment of the antigen represents an epitope sequence which can be recognised by the corresponding autoantibody. The size or type of the epitope is not limited as long as it can be recognised by the autoantibody. Details regarding the specific tumour associated antigens from which the autoantibodies of the present invention are derived are described below.

The antigen, or antigenic part thereof, which may be utilised in the detection methods described herein can be prepared using methods well known in the art. For example, recombinant DNA techniques may be used wherein a DNA molecule encoding the antigen, or part thereof, can be genetically engineered into an appropriate expression vector for large scale preparation of the antigen. It may also be advantageous to engineer fusion proteins that can facilitate labelling, immobilization or detection of the antigen. Many methods are also disclosed in standard molecular biology text books such as Green MR and Sambrook J, *Molecular Cloning: A Laboratory Manual* (4th edition), Cold Spring Harbor Laboratory Press, 2012. Alternatively, the antigen may be purified from natural sources, e.g. purified from cells using protein separation techniques well known in the art. Such purification techniques may include, but are not limited to molecular sieve chromatography and/or ion exchange chromatography.

In some embodiments, the agent may be an antibody which specifically binds to the autoantibody. The term "antibody" as used herein is used in the broadest sense and encompasses intact polyclonal antibodies, intact monoclonal antibodies, antibody fragments (such as linear antibodies, single-chain antibody molecules, Fc or Fc' peptides, Fab, Fab', F(ab')2, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be one of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, and the like.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined for example by Kabat et al., 1991 (Sequences of Proteins of Immunological Interest, Fifth Edition, U.S. Department of Health and Human Services, U.S. Government Printing Office).

Antibodies exist as intact immunoglobulins or as a number of well-characterized fragments produced by digestion with various peptidases. Therefore, for example, pepsin digests an antibody below the disulfide linkages in the hinge region to produce F(ab)'2, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region. While various antibody fragments are defined in terms of the digestion of an intact antibody, a person skilled in the art would appreciate that such fragments may be synthesized de novo either chemically or by using recombinant DNA methodology. Therefore, the term antibody, as used herein, also includes antibody fragments either produced by the modification of whole antibodies, or those synthesized de novo using recombinant DNA methodologies (e.g. single chain Fv) or those identified using phage display libraries (see for example McCafferty et al., 1990, Nature 348:552-554).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g. an enzyme, toxin, hormone, growth factor, drug, etc.; or (b) the variable region, or a portion thereof, is altered, replaced or exchanged with a variable region having a different or altered antigen specificity. The chimeric antibodies may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer (H2 L2) formed by two HL dimers associated through at least one disulfide bridge. A polyvalent chimeric antibody is based on an aggregation of chains.

In some embodiments, the antibody may be a humanised antibody. A "humanised" antibody is an antibody that retains the reactivity of a non-human antibody while being less immunogenic in humans. This can be achieved, for example, by retaining the non-human CDR regions and replacing the remaining parts of the antibody with their human counterparts. See for example Morrison et al., 1984, *Proc. Natl. Acad. Sci. USA*, 81: 6851-6855; Morrison and Oi, 1988, *Adv. Immunol.*, 44: 65-92; Verhoeyen et al., 1988, *Science*, 239: 1534-1536; Padlan, 1991, *Molec. Immun.*, 28: 489-498; and Padlan, 1994, *Molec. Immun.*, 31: 169-217.

In some embodiments, the antibody may be a fully human antibody. As would be understood by a person skilled in the art, a fully human antibody is an antibody in which both the variable and constant regions are of human origin. Methods for producing or identifying such antibodies are described below.

Additional antibody types are also contemplated by the present invention. These include antibodies sourced from a non-mammalian animal such as a cartilaginous fish (e.g. sharks) or modified human protein scaffolds that provide functionality similar to shark antibodies, such as i-bodies. Shark antibodies are also called Ig new antigen receptors (IgNARs). They are disulphide-bonded homodimers consisting of five constant domains (CNAR), one variable domain (VNAR), and no light chains (Greenberg et al., 1995, *Nature* 374: 168-173; Nuttall et al., 2001, *Mol. Immunol.*, 38: 313-326; Diaz et al., 2002, *Immunogenetics* 54: 501-512; and Nuttall et al., 2003, *Eur. J. Biochem.*, 270: 3543-3554). Antibodies sourced from camels (camelid antibodies), dromedaries and llamas are also contemplated by the present invention. Such antibodies consist of only two heavy chains and are devoid of light chains. Due to the heavy chain dimer structure of camelid and shark antibodies, they are sometimes termed "heavy-chain mini-antibodies" (mnHCAbs) or "mini-antibodies" (mnAbs) (Holliger and Hudson, 2005, *Nat. Biotechnol.*, 23(1): 1126-1136). Without the light chain, these antibodies bind to their antigens by a single domain—the variable antigen binding domain of the heavy chain immunoglobulin, referred to as Vab (camelid antibodies) or V-NAR (shark antibodies).

Affibodies are also contemplated by the present invention. Affibody molecules are a class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (Nord K et al., 1997, *Nat. Biotechnol.*, 15: 772-777; Ronmark J et al., 2002, *Eur. J. Biochem.*, 269: 2647-2655). Further details about affibodies and methods of production thereof are also disclosed in U.S. Pat. No. 5,831,012.

Antibodies for any of the methods and applications referred to herein can be produced according to well-established techniques in the art, for example by immunizing animals with one or more of the ANXA1, ARP3, SAHH, SERPH, ARAP1, OTUB1, ATP1A1, UBA1 and CFAH antigens. Alternatively, given that the amino acid sequence of these antigens is known, the relevant polypeptide can be synthesized and used to generate antibodies by methods well-known in the art. For example, monoclonal antibodies to one or more of the antigens may be prepared using any technique which provides for the production of antibody molecules by continuous cell lines in culture. These include, but are not limited to, the hybridoma technique, the human B-cell hybridoma technique, and the EBV-hybridoma technique (for example, see Kohler et al., 1975, *Nature* 256: 495-497; Kozbor et al., 1985, *J. Immunol. Methods* 81:31-42; Cote et al., 1983, *Proc. Natl. Acad. Sci. USA* 80: 2026-2030; and Cole et al., 1984, *Mol. Cell Biochem.* 62: 109-120).

Antibodies may also be produced by inducing in vivo production in the lymphocyte population or by screening immunoglobulin libraries or panels of highly specific binding reagents as disclosed in the literature (for example, see Orlandi et al., 1989, *Proc. Natl. Acad. Sci. USA* 86: 3833-3837; and Winter and Milstein, 1991, *Nature* 349: 293-299). Antibodies may also be generated using phage display. For example, functional antibody domains are displayed on the surface of phage particles that carry the polynucleotide sequences encoding them. Such phage can be utilized to display antigen-binding domains expressed from a repertoire or combinatorial antibody library (e.g. human or murine). Phage expressing an antigen binding domain that binds one or more of the aforementioned antigens can be selected or identified using the relevant antigen, e.g. using labelled antigen or a portion thereof. Phage used in these methods are typically filamentous phage including fd and MI 3 binding domains expressed from phage with Fab, Fv or disulfide stabilised Fv antibody domains recombinantly fused to either the phage gene III or gene VIII protein. Examples of phage display methods that can be used to make the antibodies may include those disclosed in Brinkman et al., 1995, *J. Immunol. Methods* 182: 41-50; Ames et al., 1995, *J. Immunol. Methods* 184: 177-186; Kettleborough et al., 1994, *Eur. J. Immunol.* 24: 952-958; Persic et al., 1997, *Gene* 187: 9-18; Burton et al., 1994, *Advances in Immunology* 57: 191-280; PCT application number PCT/GB91/01134; PCT publications numbers WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *Proc. Natl. Acad. Sci. USA* 90: 7995-7999; and Skerra et al., 1988, *Science* 240: 1038-1040.

Antibody fragments which contain specific binding sites for the one or more aforementioned antigens may be generated using standard techniques known in the art. For example, F(ab')2 fragments may be produced by pepsin digestion of a Flightless I antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (for example, see Huse et al., 1989, *Science* 246: 1275-1281).

Fully human antibodies may be produced using a number of techniques. These include using display technologies as mentioned above in which human antibodies or antibody fragments are displayed on the surface of a phage for example. In another method (Lonberg N, 2008, *Handb. Exp. Pharmacol.*, 69-97), first generation human antibodies to one or more of the ANXA1, ARP3, SAHH, SERPH, ARAP1, OTUB1, ATP1A1, UBA1 and CFAH antigens may be produced by utilising transgenic animals that produce antibodies from human genes. When challenged with the antigen, or an oligopeptide, peptide, or fragment thereof, these animals produce human antibodies avoiding the humanisation steps. Human antibodies can also be produced from B cells isolated from humans using a technique described in Crowe J E Jr, 2009, *Vaccine* 27: 47-51. Other techniques for human antibody production are described in PCT international publication number WO 2013/168150 and Duvall M et al., 2011, *mAbs* 3(2): 203-208, amongst others. For example, Duvall et al utilises technology which produces human IgG antibody libraries from naïve B cells isolated from human tonsil tissue. The antibodies are produced from human genes and are therefore 100% human antibodies.

Methods for detecting the presence, or testing for the presence, of an autoantibody in a subject using an agent referred to above can be achieved a number of ways. Exemplary methods include, but are not limited to, protein microarrays, mass spectrometry-based techniques (including liquid chromatography coupled to tandem mass spectrometry (LC-MS/MS), nano LC-MS/MS, matrix-assisted laser desorption/ionization mass spectrometry (MALDI-MS) as described in WO 2009/004576 (including surface enhanced laser desorption/ionization mass spectrometry (SELDI-MS), especially surface-enhanced affinity capture (SEAC), surface-enhanced need desorption (SEND) or surface-enhanced photo label attachment and release (SEPAR)), matrix-assisted laser desorption/ionization time-of-flight (MALDI-TOF) mass spectrometry, antibody-based (immunoassay-based) testing techniques (including Western blotting, immunoblotting, enzyme-linked immunosorbent assay (ELISA), "sandwich" immunoassays, radioimmunoassay (RIA), immunoprecipitation and dissociation-enhanced lanthanide fluoro immuno assay (DELFIA), precipitin reactions, gel diffusion precipitin reactions, immunodiffusion assays, immunoradiometric assays and protein A immunoassays), proteomics techniques, surface plasmon resonance (SPR), versatile fibre-based SPR, chemiluminescence, fluorescent polarization, phosphorescence, immunohistochemistry, immunofluorescence, microcytometry, microscopy, fluorescence activated cell sorting (FACS), and flow cytometry. Some of these techniques are described in further detail below.

The majority of the aforementioned techniques rely on the agent being detectably labelled. The agent is typically labelled by covalently or non-covalently combining the agent with a substance or ligand that provides, or enables the generation of, a detectable signal. Some examples include, but are not limited to, radioactive isotopes, enzymes, fluorescent substances, luminescent substances, ligands, microparticles, redox molecules, substrates, cofactors, inhibitors, magnetic particles and the like. Examples of the radioactive isotopes include, but are not limited to, $^{3}$H, $^{12}$C, $^{13}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. For example, when the agent is an antigen from which the autoantibody was derived, the isotope-coded protein labeling (ICPL) technique can be used to label primary amines found in proteins with $^{12}$C-nicotinoyloxysuccinimide and/or $^{13}$C-nicotinoyloxysuccinimide. Examples of enzymes available as detection labels include, but are not limited to, β-glucuronidase, β-glucosidase, β-galactosidase, urease, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescin, isothiocyanate, rhodamine, phycoerythrin, phycocyanin, allophycocyanin, o-phthaldehyde and fluorescamin. Examples of luminescent substances include, but are not limited to, acridinium esters, luciferin and luciferase. Examples of ligands include, but are not limited to, biotin and its derivatives. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$.

When the agent is an antigen from which the one or more autoantibodies of the present invention were derived, antigen-autoantibody interactions can be detected by using a number of the methods as described above. In general, these methods rely on contacting a sample derived from a subject with a sample containing the corresponding antigen, or part thereof, under conditions which allow an immunospecific antigen-antibody binding reaction to occur. The antigen may be present in solution, or may be anchored to a solid support such that chip-based or microarray detection methods may be utilised. In general, in a chip-based or microarray approach, a peptide having an amino acid sequence representing all, or a portion, of the antigen occupies a known location on a substrate. A sample that has been obtained from a subject of interest is then hybridized to the chip or microarray and the binding of the corresponding autoantibody (if present in the sample) to the antigen is detected using the techniques referred to above, for example a mass spectrometry technique or an immunoassay-based technique. Many protein microarrays are described in the art, including for example protein biochips produced by Origene Technologies (Rockville, MD), Zyomyx (Hayward, CA), Invitrogen (Carlsbad, CA), Biacore (Uppsala, Sweden) and Procognia (Berkshire, UK). Examples of such protein biochips are described in the following patents or published patent applications: U.S. Pat. Nos. 6,225,047, 6,537,749, 6,329,209, and 5,242,828, and PCT International Publication Nos. WO 00/56934 and WO 03/048768.

As indicated above, the presence of an autoantibody of interest can also be measured by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. The mass spectrometer may be a laser desorption/ionization (LDI) mass spectrometer. In laser desorption/ionization mass spectrometry, the autoantibody or autoantibodies to be detected are placed on the surface of a mass spectrometry probe, a device adapted to engage a probe interface of the mass spectrometer and to present the autoantibody or autoantibodies to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of autoantibodies by LDI can take the form of MALDI or of SELDI, as described below.

The SELDI method is described, for example, in U.S. Pat. Nos. 5,719,060 and 6,225,047, and relates to a method of desorption/ionization gas phase ion spectrometry (e.g. mass spectrometry) in which an analyte (in this instance one or more of the autoantibodies to be detected) is captured on the surface of a SELDI mass spectrometry probe. SELDI also encompasses affinity capture mass spectrometry, surface-enhanced affinity capture (SEAC) and immuno-capture mass spectrometry (icMS) as described by Penno M A et al., 2012, Res. Vet. Sci., 93: 611-617. These platforms involve the use of probes that have a material on the probe surface that can capture an autoantibody through a non-covalent affinity interaction (adsorption) between the material and the autoantibody. The material is variously called an "adsorbent," a "capture reagent," an "affinity reagent" or a "binding moiety." Such probes can be referred to as "affinity capture probes" and as having an "adsorbent surface." The capture reagent can be any material capable of binding an autoantibody. The capture reagent is attached to the probe surface by physisorption or chemisorption. The probes, which may take the form of a functionalised biochip or magnetic bead, may have the capture reagent already attached to the surface, or the probes are pre-activated and include a reactive moiety that is capable of binding the capture reagent, e.g. through a reaction forming a covalent or coordinate covalent bond. Epoxide and acyl-imidizole are useful reactive moieties to covalently bind protein capture reagents such as antibodies or cellular receptors. Nitrilotriacetic acid and iminodiacetic acid are useful reactive moieties that function as chelating agents to bind metal ions that interact non-covalently with histidine containing proteins. Adsorbents are generally classified as chromatographic adsorbents and biospecific adsorbents.

A chromatographic adsorbent refers to an adsorbent material typically used in chromatography. Chromatographic adsorbents include, for example, ion exchange materials, metal chelators (e.g. nitrilotriacetic acid or iminodiacetic acid), immobilized metal chelates, hydrophobic interaction adsorbents, hydrophilic interaction adsorbents, dyes, simple biomolecules (e.g. nucleotides, amino acids, simple sugars and fatty acids) and mixed mode adsorbents (e.g. hydrophobic attraction/electrostatic repulsion adsorbents). One method which uses a chromatographic adsorbent is liquid chromatography coupled to tandem mass spectrometry (LC-MS/MS), including nano-LC-MS/MS. The technique of nano-LC-MS/MS is described in Gaspari M and Cuda G, 2011, Nanoproteomics: Methods and Protocols, Methods in Molecular Biology, 790: 115-126.

A biospecific adsorbent refers to an adsorbent comprising a biomolecule, e.g. a nucleic acid molecule (e.g. an aptamer), a polypeptide, a polysaccharide, a lipid, a steroid or a conjugate of these (e.g. a glycoprotein, a lipoprotein, a glycolipid, a nucleic acid (e.g. DNA-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target autoantibody than chromatographic adsorbents.

In general, a probe with an adsorbent surface is contacted with a sample being tested for a period of time sufficient to allow the autoantibody or autoantibodies under investigation to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In a further approach, the one or more autoantibodies under investigation can be captured with a solid-phase bound immuno-adsorbent that has antibodies that specifically bind to the or each autoantibody. After washing the adsorbent to remove unbound material, the one or more autoantibodies are eluted from the solid phase and detected by applying them to a biochip that binds the autoantibodies.

An autoantibody under investigation which is bound to the substrate is detected in a gas phase ion spectrometer such as a time-of-flight mass spectrometer. The autoantibody is ionized by an ionization source such as a laser, the generated ions are collected by an ion optic assembly, and then a mass analyzer disperses and analyzes the passing ions. The detector then translates information of the detected ions into mass-to-charge ratios. Detection of an autoantibody will typically involve detection of signal intensity. Thus, both the quantity and mass of the autoantibody can be determined.

Another method of laser desorption mass spectrometry is called surface-enhanced neat desorption (SEND). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. The energy absorbing molecule may be incorporated into a linear or cross-linked polymer, e.g. a polymethacrylate. For example, the composition can be a co-polymer of α-cyano-4-methacryloyloxy-cinnamic acid and acrylate. Alternatively, the composition may be a co-polymer of α-cyano-4-methacryloyloxycinnamic acid, acrylate and 3-(tri-ethoxy)silyl propyl methacrylate, or may be a co-polymer of α-cyano-4-methacryloyloxycinnamic acid and octadecylmethacrylate ("C1 8 SEND"). SEND is further described in U.S. Pat. No. 6,124,137 and PCT International Publication No. WO 03/64594.

SEAC/SEND is a version of laser desorption mass spectrometry in which both a capture reagent and an energy absorbing molecule are attached to the sample presenting surface. SEAC/SEND probes therefore allow the capture of autoantibodies under investigation through affinity capture and ionization/desorption without the need to apply external matrix. The CI 8 SEND biochip is a version of SEAC/

SEND, comprising a CI 8 moiety which functions as a capture reagent, and a CHCA moiety which functions as an energy absorbing moiety.

Another version of LDI is called surface-enhanced photolabile attachment and Release (SEPAR). SEPAR involves the use of probes having moieties attached to the surface that can covalently bind an autoantibody, and then release the autoantibody through breaking a photolabile bond in the moiety after exposure to light, e.g. to laser light. SEPAR and other forms of SELDI are readily adapted to detecting an autoantibody, as required by the methods of the present invention.

MALDI is a traditional method of laser desorption/ionization. In one MALDI method, the sample to be tested is mixed with matrix and deposited directly on a MALDI chip. Depending on the sample being tested, the autoantibody under investigation is preferably first captured with biospecific (e.g. its corresponding antigen) or chromatographic materials coupled to a solid support such as a resin (e.g. in a spin column). Specific affinity materials that may bind the autoantibody being detected are described above. After purification on the affinity material, the autoantibody under investigation is eluted and then detected by MALDI.

Analysis of autoantibodies by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing using specialized software. Data processing typically includes TOF-to-M/Z transformation to generate a mass spectrum, baseline subtraction to eliminate instrument offsets and high frequency noise filtering to reduce high frequency noise.

Data generated by desorption and detection of autoantibodies can be analyzed with the use of a programmable digital computer. The computer program analyzes the data to indicate the number of autoantibodies detected, and optionally the strength of the signal and the determined molecular mass for each autoantibody detected. Data analysis can include steps of determining signal strength of an autoantibody and removing data deviating from a predetermined statistical distribution. For example, the observed peaks can be normalized, by calculating the height of each peak relative to some reference. The computer can transform the resulting data into various formats for display. The standard spectrum can be displayed, but in one useful format only the peak height and mass information are retained from the spectrum view, yielding a cleaner image and enabling autoantibodies with nearly identical molecular weights to be more easily seen. Using any of these formats, one can readily determine whether a particular autoantibody is present in a sample.

Analysis generally involves the identification of peaks in the spectrum that represent signal from an autoantibody. Peak selection can be done visually, but commercial software can be used to automate the detection of peaks. In general, this software functions by identifying signals having a signal-to-noise ratio above a selected threshold and labelling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to an autoantibody under investigation. The software also can subject the data regarding observed autoantibody peaks to a classification tree or ANN analysis, to determine whether an autoantibody peak or combination of autoantibody peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

A further technique for detecting the presence of an autoantibody involves the versatile fibre-based surface plasmon resonance (VeSPR) biosensor, as described in PCT International Publication No. WO 2011/113085. Traditional SPR is a well-established method for label-free bio-sensing that relies on the excitation of free electrons at the interface between a dielectric substrate and a thin metal coating. The condition under which the incoming light couples into the plasmonic wave depends on the incidence angle and the wavelength of the incoming light as well as the physical properties (dielectric constant/refractive index) of the sensor itself and the surrounding environment. For this reason, SPR is sensitive to even small variations in the density (refractive index) in the close vicinity of the sensor, and does not require the use of fluorescent labels. The small variation of refractive index induced by the binding biomolecules such as autoantibodies onto the sensor surface, can be measured by monitoring the coupling conditions via either the incidence angle or the wavelength of the incoming light. Existing SPR systems use the Krestchmann prism configuration where one side of the prism is coated with a metal such as gold or silver that can support a plasmonic wave. Alternative SPR architectures have been developed based on optical fibres with the metallic coating deposited around a short section of the fibre. This approach reduces the complexity and cost of such sensors, opening a pathway to distinctive applications such as dip sensing. The material at the sensor surface is probed by monitoring the wavelength within a broad spectrum that is absorbed due to coupling to the surface plasmon. These techniques suffer from practical limitations associated with the need for careful temperature calibration, causing difficulty in analysing large numbers of samples consistently. A novel and powerful variant of an optical-fibre based SPR sensor, known as VeSPR, has been developed recently. VeSPR has a number of demonstrated advantages over existing SPR techniques including: (i) higher signal-to-noise ratio thus higher sensitivity; (ii) self-referencing of the transducing signal thus avoiding expensive/bulky temperature control; and (iii) the ability to perform multiplexed detection of different analytes using a single fibre.

As indicated above, an autoantibody can be detected by use of an agent that binds/interacts with the autoantibody in an indirect manner. With reference to the antibody-based detection methods described above, binding of a primary antibody specific for the autoantibody under investigation can be detected through use of a secondary antibody or reagent to the primary antibody. In effect, it is the binding or interaction of the secondary antibody or reagent with the primary antibody that is detected. The secondary antibody or reagent can be detected using the aforementioned methods.

Furthermore, in certain instances it may be advantageous to detect the presence of an autoantibody by using an intermediary ligand that has binding affinity for the antigen or for the autoantibody if present in the sample, for example reactivity to the Fc region of the autoantibody or having reactivity to a region of the antigen different to the binding region of the autoantibody. In these cases, the intermediary agent can be linked to a detectable label or marker molecule as described above. The ligand is itself often an antibody which may thus be termed a secondary antibody. Typically, the antigen-autoantibody is contacted with the labelled ligand or secondary antibody under conditions effective and for a period of time sufficient to allow the formation of secondary immune complexes. The secondary immune complexes are then generally washed to remove any unbound labelled ligand or secondary antibody, and the remaining label in the secondary immune complex is then detected.

In the subject, the presence of the one or more ovarian cancer-associated autoantibodies of the present invention may be detected directly in the subject, or in an alternative embodiment, their presence may be detected in a sample obtained from a subject. It is to be made clear that the sample obtained from the subject that is analysed by the methods of the present invention may have previously been obtained from the subject, and, for example, has been stored in an appropriate repository. In this instance, the sample would have been obtained from the subject in isolation of, and therefore separate to, the methods of the present invention.

The sample which is obtained from the subject may include, but is not limited to, serum, whole blood, blood plasma, serum, whole blood, blood plasma, saliva, buccal swab, cervical pap smears, stool, urine, bladder washing, uterine washing, sputum, lymphatic fluid, cerebrospinal fluid, semen, and a tissue sample from one or both ovaries or metastatic tumour tissue of the subject. In certain circumstances, the sample may be manipulated in any way after procurement, such as by treatment with reagents, solubilization, or enrichment for certain components, such as the relevant autoantibody under investigation.

In one embodiment, the sample is a serum sample obtained from the subject. Serum is derived from blood plasma which is the yellow liquid component of blood, in which the blood cells in whole blood would normally be suspended. It makes up about 55% of the total blood volume. It is mostly water (90% by volume) and contains dissolved proteins, glucose, clotting factors, mineral ions, hormones and carbon dioxide. Blood plasma is prepared by spinning a tube of fresh blood in a centrifuge until the blood cells fall to the bottom of the tube. The blood plasma is then poured or drawn off. Blood plasma, preferably supplemented with a clotting inhibitor, e.g. heparin or EDTA, has a density of approximately 1.025 kg/l. Blood serum is blood plasma without fibrinogen or the other clotting factors (i.e., whole blood minus both the cells and the clotting factors).

The inventors have established that the autoantibodies of the present invention are detectable at the early stages of ovarian cancer progression, and as early as stage I of the cancer. In the more advanced stages of the disease, the level of the autoantibodies in the affected subject would be expected to be higher than the level of the autoantibodies in a subject with less advanced cancer due to the larger number of tumour cells (and therefore corresponding tumour associated antigen) present in the subject with advanced cancer.

Accordingly, in a third aspect the present invention provides a method of assessing progression or recurrence of ovarian cancer in a subject, the method including the step of detecting the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the method includes:

(a) detecting the level of the one or more ovarian cancer-associated autoantibodies in the subject;

(b) comparing the level of the one or more ovarian cancer-associated autoantibodies in the subject to a reference level for the or each ovarian cancer-associated autoantibody; and (c) assessing the progression or recurrence of ovarian cancer in the subject on the basis of the comparison.

Methods for detecting the presence or level of the one or more ovarian cancer-associated autoantibodies in the subject have been described in detail above. As indicated above, the one or more ovarian cancer-associated autoantibodies of the present invention may be detected directly in the subject, or in an alternative embodiment, their presence may be detected in a sample obtained from a subject. The sample may be one or more of those referred to herein.

Once the level of the one or more autoantibodies has been detected in the subject, or in a sample obtained from the subject, the level is compared to a reference level for each autoantibody. The reference level for a particular autoantibody is an amount of the autoantibody that is associated with a particular stage of ovarian cancer progression (i.e. stage I, II, III or IV). A reference level for each autoantibody may be derived from at least one subject having ovarian cancer at a defined stage of progression, and is preferably derived from an average of such subjects (e.g. n=2 to 100 or more).

In some embodiments of the present invention, the presence or level of the one or more autoantibodies is detected at more than one time points. Such "serial" sampling is well suited, for example, to monitoring the progression of ovarian cancer. Serial sampling can be performed for any desired timeline, such as monthly, quarterly (i.e. every three months), semi-annually, annually, biennially, or less frequently. The comparison between the detected level in the subject and the reference level may be carried out each time a new sample is measured, or the data relating to levels may be held for less frequent analysis.

In some embodiments of the third aspect of the invention, a level of the one or more ovarian cancer-associated autoantibodies in the subject that is higher than the reference level for the or each ovarian cancer-associated autoantibody is indicative of the progression of ovarian cancer in the subject.

In one embodiment of the third aspect of the invention, the subject is undergoing treatment for the ovarian cancer. The treatment may be a conventional therapy such as chemotherapy or radiotherapy, or the treatment may be an alternative therapy. In an alternative embodiment, the subject may not be undergoing treatment at all, either by choice or because the subject has subsequently been considered disease-free following therapy.

The method according to the third aspect of the present invention can therefore be used to monitor the efficacy of treatment regimens for ovarian cancer with the ultimate aim of disease elimination. In such circumstances, success of the treatment can be measured as a reduction or elimination of the one or more autoantibodies from the affected subject. Accordingly, in some embodiments, a level of the one or more ovarian cancer-associated autoantibodies in the subject that is lower than the reference level for the, or each, autoantibody is indicative of the regression of ovarian cancer in the subject. In circumstances where elimination or near elimination of ovarian cancer in the subject has been achieved, the reference level for the or each autoantibody can be considered a level which is known to be found in a subject not suffering from ovarian cancer (a "normal" subject in the context of the present invention). In this instance, a reference level for the or each autoantibody may be derived from at least one normal subject and is preferably derived from an average of normal subjects (e.g. n=2 to 100 or more), wherein the subject or subjects have no prior history of ovarian cancer. A reference level for the, or each, autoantibody can also be obtained from one or more normal samples from a subject suspected to have, or which has, ovarian cancer. For example, a reference level for the or each autoantibody may be obtained from at least one normal sample and is preferably obtained from an average of normal samples (e.g. n=2 to 100 or more), wherein the subject is suspected of having, or which has, ovarian cancer.

As indicated above, the method according to the third aspect of the present invention can also be used to assess or monitor recurrence of ovarian cancer in a subject who has previously been considered disease-free following therapy. Accordingly, in some embodiments, a level of the one or more ovarian cancer-associated autoantibodies in the subject that is higher than the reference level for the, or each, autoantibody is indicative of recurrence of ovarian cancer in the subject. In circumstances where elimination or near elimination of ovarian cancer in the subject has been maintained in the subject, the reference level for the, or each, autoantibody can be considered a level which is known to be found in a subject not suffering from ovarian cancer as indicated above.

In some embodiments, the method according to the third aspect of the invention may be used to perform clinical trials of a new drug, as well as to monitor the progress of a subject on the drug. Therapy or clinical trials involve administering the drug being tested in a particular regimen. The regimen may involve a single dose of the drug or multiple doses of the drug over time. The doctor or clinical researcher monitors the effect of the drug on the subject over the course of administration. If the drug has a pharmacological impact on ovarian cancer, the level of the aforementioned autoantibodies will be lower than the reference level for the autoantibodies. Therefore, the trending of the levels of the autoantibodies can be monitored in the subject during the course of treatment. The level of the one or more autoantibodies can be determined using the methods described in detail above. One embodiment of this method involves determining the levels of the aforementioned autoantibodies for at least two different time points during a course of drug therapy, e.g. a first time and a second time, and comparing the change in levels of the autoantibodies, if any. For example, the level of the autoantibodies can be measured before and after drug administration or at two different time points during drug administration. The effect of therapy is determined based on these comparisons. If a treatment is effective, the level of the aforementioned autoantibodies will be lower than the reference level for the autoantibodies, while if treatment is ineffective, the level of the aforementioned autoantibodies will remain the same or will be higher than the reference level for the biomarkers. For example, if the stage of ovarian cancer in the subject at the start of the clinical trial is stage II then the reference level of the, or each, autoantibody will correspond to the level of the or each autoantibody at this stage of the cancer. A successful treatment will be observed when the level of the, or each, autoantibody in the subject becomes lower than the reference level.

In a fourth aspect, the present invention provides a method of screening a candidate therapeutic agent useful for treating ovarian cancer, the method including the step of assaying the candidate therapeutic agent for activity in reducing a level of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, the method includes:

(a) administering the candidate therapeutic agent to the subject;

(b) detecting the level of the one or more ovarian cancer-associated autoantibodies in the subject; and (c) comparing the level of the one or more ovarian cancer-associated autoantibodies in the subject to the level of the one or more ovarian cancer-associated autoantibodies in an untreated subject having ovarian cancer, wherein if the level of the one or more ovarian cancer-associated autoantibodies in the subject is lower than the level of the one or more ovarian cancer-associated autoantibodies in the untreated subject, the candidate therapeutic agent is useful for treating ovarian cancer.

The level of the one or more ovarian cancer-associated autoantibodies can be detected in the subject using the methods described above. In some embodiments, the level of the one or more autoantibodies is detected in a sample obtained from the subject. The sample may be one or more of those described above.

Screening assays may be performed in vitro and/or in vivo. For example, prospective agents may be screened to identify candidate therapeutic agents for the treatment of ovarian cancer in a cell-based assay. In this regard, each prospective agent is incubated with cultured cells (for example cells obtained from an ovary of a normal subject or from a subject suffering from ovarian cancer, or cell lines derived from a normal or affected subject), and the level of one or more of the autoantibodies is measured. Accordingly, in one embodiment of the fourth aspect of the invention, the method includes:

(a) exposing the candidate therapeutic agent to a cell expressing one or more of the autoantibodies;

(b) measuring for a change in the level of the or each autoantibody in the cell; and (c) comparing the level of the or each autoantibody in the subject to a reference level for the or each autoantibody, wherein if the level of the or each autoantibody is lower than the reference level for the or each autoantibody, the candidate therapeutic agent is useful for treating ovarian cancer in a subject.

The reference level for the or each autoantibody may be determined as described above.

In another example, candidate therapeutic agents may be screened in organ culture-based assays. In this regard, each prospective agent is incubated with either a whole organ or a portion of an organ (such as a portion of an ovary of a normal of affected subject) derived from a non-human animal and modulation of the level of the target autoantibody is measured.

As set out above, the methods of the aforementioned aspects of the invention involve detecting the presence or level of one or more autoantibodies selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH. Details of the tumour proteins (tumour associated antigens) from which these autoantibodies were derived, particularly with respect to amino acid and nucleic acid sequence information, may be accessed from the GenBank database at the National Center for Biotechnology Information (ncbi.nlm.nih.gov). Particular details are provided below.

ANXA1 (Annexin A1)

The ANXA1 protein belongs to the annexin family of proteins and is a calcium/phospholipid-binding protein that promotes membrane fusion and has an involvement in exocytosis. The ANXA1 protein regulates phospholipase A2 activity and is suspected to bind from two to four calcium ions with high affinity. Since phospholipase A2 is required for the biosynthesis of the potent mediators of inflammation, prostaglandins, and leukotrienes, ANXA1 may have potential anti-inflammatory activity. The ANXA1 gene is also known as Annexin I, Annexin A1, ANX1, Annexin-1, Calpactin II, Calpactin-2, Chromobindin-9, Lipocortin I, Phospholipase A2 Inhibitory Protein, LPC1 and p35. The GenBank Gene ID number for human ANXA1 is 301, and the human ANXA1 gene encodes a protein represented by GenBank Accession Number NP_00069.1. The nucleotide sequence encoding the ANXA1 protein is represented by GenBank Accession Number NM_000700.1. Details of the amino acid sequence encoded by ANXA1 can also be accessed from the UniProt database wherein the UniProt ID for human ANXA1 is P04083.

ARP3 (Actin-Related Protein 3)

The ARP3 protein has been shown to function as an ATP-binding component of the Arp2/3 complex which is involved in the regulation of actin polymerization. Together with an activating nucleation-promoting factor (NPF), ARP3 mediates the formation of branched actin networks. The ARP3 gene is also known as Actin-Like Protein 3, ACTR3 and Actin-Related Protein 3 homolog (yeast). The GenBank Gene ID number for human ARP3 is 10096, and the human ARP3 gene encodes two protein variants as represented by GenBank Accession Numbers NP_005712.1 (isoform 1) and NP_001264069.1 (isoform 2). The nucleotide sequences encoding these variants are represented by GenBank Accession Numbers NM_005721.4 (isoform 1) and NM_001277140.1 (isoform 2). Details of the amino acid sequences encoded by ARP3 can also be accessed from the UniProt database (uniprot.org) wherein the UniProt ID for isoform 1 is P61158 and for isoform 2 is B4DXW1.

SAHH (Adenosylhomocysteinase)

The SAHH protein belongs to the adenosylhomocysteinase family. It catalyzes the reversible hydrolysis of S-adenosylhomocysteine (AdoHcy) to adenosine (Ado) and L-homocysteine (Hcy). Therefore, it regulates the intracellular S-adenosylhomocysteine (SAH) concentration thought to be important for transmethylation reactions. The SAHH gene is also known as adenosylhomocysteinase, S-adenosylhomocysteine hydrolase, S-adenosyl-L-homocysteine hydrolase, and AHCY. The GenBank Gene ID number for human SAHH is 191, and the human SAHH gene encodes two protein variants as represented by GenBank Accession Numbers NP_000678.1 (isoform 1) and NP_001155238.1 (isoform 2). The nucleotide sequences encoding these variants are represented by GenBank Accession Numbers NM_000687.2 (isoform 1) and NM_001161766.1 (isoform 2). Details of the amino acid sequences encoded by SAHH can also be accessed from the UniProt database wherein the UniProt ID for human SAHH (including each variant) is P23526.

SERPH (Serpin H1)

The SERPH gene encodes a member of the serpin superfamily of serine proteinase inhibitors. The encoded protein is localized to the endoplasmic reticulum and plays a role in collagen biosynthesis as a collagen-specific molecular chaperone. The SERPH gene is also known as Serpin H1 precursor, SERPINH1, Colligin-1, Colligin-2, Arsenic-transactivated protein 3 (AsTP3), serine (or cysteine) proteinase inhibitor, clade H (heat shock protein 47), member 1, (collagen binding protein 1)(CBP1), serine (or cysteine) proteinase inhibitor, clade H (heat shock protein 47), member 2, (collagen binding protein 2)(CBP2), gp46, 47 kDa heat shock protein (HSP47), Ol10, PIG14, PPROM, Rheumatoid arthritis antigen A-47 (RA-A47) and SerpinH2. The GenBank Gene ID number for human SERPH is 871, and the human SERPH gene encodes two protein variants as represented by GenBank Accession Numbers NP_001193943.1 (variant 1) and NP_001226.2 (variant 2). The nucleotide sequences encoding these variants are represented by GenBank Accession Numbers NM_001207014.1 (variant 1) and NM_001235.3 (variant 2). Details of the amino acid sequences encoded by SERPH can also be accessed from the UniProt database wherein the UniProt ID for human SERPH (including each variant) is P50454.

ARAP1 (ArfGAP with RhoGAP Domain, Ankyrin Repeat and PH Domain 1)

The protein encoded by the ARAP1 gene contains SAM, ARF-GAP, RHO-GAP, ankyrin repeat, RAS-associating, and pleckstrin homology (PH) domains. In vitro, ARAP1 displays RHO-GAP and phosphatidylinositol (3,4,5) trisphosphate (PIP3)-dependent ARF-GAP activity. ARAP1 associates with the Golgi, and the ARF-GAP activity mediates changes in the Golgi and the formation of filopodia. The ARAP1 protein is thought to regulate the cell-specific trafficking of a receptor protein involved in apoptosis. ARAP1 is also known as CENTD2, cnt-d2, Centaurin-delta-2, Centaurin delta 2 and ARF-GAP, RHO-GAP, ankyrin repeat, and pleckstrin homology domains-containing protein 1. The GenBank Gene ID number for human ARAP1 is 116985, and the human ARAP1 gene encodes three protein variants as represented by GenBank Accession Numbers NP_056057.2 (variant 1—isoform a), NP_001035207.1 (variant 2—isoform c) and NP_001128662.1 (variant 3—isoform d). The nucleotide sequences encoding these variants are represented by GenBank Accession Numbers NM_015242.4 (variant 1), NM_001040118.2 (variant 2) and NM_001135190.1 (variant 3). Details of the amino acid sequences encoded by ARAP1 can also be accessed from the UniProt database wherein the UniProt ID for human ARAP1 (including each variant) is Q96P48.

OTUB1 (Ubiquitin Thioesterase)

OTUB1 is a member of the OTU (ovarian tumor) superfamily of predicted cysteine proteases. The encoded protein is a highly specific ubiquitin iso-peptidase, and cleaves ubiquitin from branched poly-ubiquitin chains but not from ubiquitinated substrates. It interacts with another ubiquitin protease and an E3 ubiquitin ligase that inhibits cytokine gene transcription in the immune system. It is proposed to function in specific ubiquitin-dependent pathways, possibly by providing an editing function for polyubiquitin chain growth. OTUB1 is also known as Otubain-1, OTB1, OTU1, HSPC263, OTU-domain Ubal-binding 1, deubiquitinating enzyme, ubiquitin-specific protease otubain 1, ubiquitin-specific-processing protease, and OTU domain-containing ubiquitin aldehyde-binding protein 1. The GenBank Gene ID number for human OTUB1 is 55611, and the human OTUB1 gene encodes two protein variants. One variant is represented by GenBank Accession Number NP_060140.2 (variant 1), while the second variant is a transcript variant that has an alternative segment in the 3' coding region, compared to variant 1, that results in a frameshift. It is not known if this second variant is actually translated into a polypeptide. The mRNA sequence of this second transcript variant is represented by GenBank Accession Number NR_003089.1. The nucleotide sequence encoding variant 1 is represented by GenBank Accession Number NM_017670.2. Details of the amino acid sequences encoded by OTUB1 can also be accessed from the UniProt database wherein the UniProt ID for human OTUB1 is Q96FW1.

ATP1A1 (Sodium/Potassium-Transporting ATPase Subunit Alpha-1)

ATP1A1 belongs to the family of P-type cation transport ATPases, and to the subfamily of Na+/K+-ATPases. Na+/K+-ATPase is an integral membrane protein responsible for establishing and maintaining the electrochemical gradients of Na and K ions across the plasma membrane. These gradients are essential for osmoregulation, for sodium-coupled transport of a variety of organic and inorganic molecules, and for electrical excitability of nerve and muscle. This enzyme is composed of two subunits, a large catalytic subunit (alpha) and a smaller glycoprotein subunit (beta). The catalytic subunit of Na+/K+-ATPase is encoded by multiple genes. The ATP1A1 gene encodes an alpha 1 subunit. ATP1A1 is also known as ATPase, Na+/K+ transporting, alpha 1 polypeptide, sodium pump 1, Na+/K+ ATPase 1, Na,K-ATPase alpha-1 subunit, sodium pump subunit alpha-1, Na+, K+ ATPase alpha subunit, Na(+)/K(+) ATPase alpha-1 subunit, Na, K-ATPase, alpha-A catalytic polypeptide, sodium-potassium-ATPase, alpha 1 polypeptide, Na,K-ATPase catalytic subunit alpha-A protein and sodium-potassium ATPase catalytic subunit alpha-1. The GenBank Gene ID number for human ATP1A1 is 476, and the human ATP1A1 gene encodes three protein variants as represented by GenBank Accession Numbers NP_000692.2 (variant 1—isoform a), NP_001153705.1 (variant 2—isoform c) and NP_001153706.1 (variant 3—isoform d). The nucleotide sequences encoding these variants are represented by GenBank Accession Numbers NM_000701.7 (variant 1), NM_001160233.1 (variant 2) and NM_001160234.1 (variant 3). Details of the amino acid sequences encoded by ATP1A1 can also be accessed from the UniProt database wherein the UniProt ID for human ATP1A1 (including each variant) is P05023.

UBA1 (Ubiquitin-Like Modifier-Activating Enzyme 1)

UBA1 catalyzes the first step in ubiquitin conjugation to mark cellular proteins for degradation. The UBA1 gene complements an X-linked mouse temperature-sensitive defect in DNA synthesis, and therefore may function in DNA repair. UBA1 is also known as A1S9, A1ST, GXP1, UBE1, A1S9T, AMCX1, POC20, SMAX2, UBA1A, UBE1X, POC20 centriolar protein homolog, ubiquitin-activating enzyme E1 homolog A, and A1S9T and BN75 temperature sensitivity complementing. The GenBank Gene ID number for human UBA1 is 7317, and the human UBA1 gene encodes two protein variants as represented by GenBank Accession Numbers NP_003325.2 (variant 1) and NP_695012.1 (variant 2). The nucleotide sequences encoding these variants are represented by GenBank Accession Numbers NM_003334.3 (variant 1) and NM_153280.2 (variant 2). Details of the amino acid sequences encoded by UBA1 can also be accessed from the UniProt database wherein the UniProt ID for human UBA1 (including each variant) is P22314.

CFAH (Complement Factor H)

The CFAH gene is a member of the Regulator of Complement Activation (RCA) gene cluster and encodes a protein with twenty short consensus repeat (SCR) domains. The CFAH protein is secreted into the bloodstream and has an essential role in the regulation of complement activation, restricting this innate defence mechanism to microbial infections. Mutations in this gene have been associated with hemolytic-uremic syndrome (HUS) and chronic hypocomplementemic nephropathy. CFAH is also known as CFH, factor H (FH), HF, H factor 1 (complement)(HF1), H factor 2 (complement)(HF2), HUS, factor H-like 1 (FHL1), AHUS1, adrenomedullin binding protein (AMBP1), ARMD4, age-related maculopathy susceptibility 1 (ARMS1), CFHL3, beta-1H, beta-1-H-globulin, and complement factor H, isoform b. The GenBank Gene ID number for human CFAH is 3075, and the human CFAH gene encodes two protein variants as represented by GenBank Accession Numbers NP_000177.2 (variant 1) and NP_001014975.1 (variant 2). The nucleotide sequences encoding these variants are represented by GenBank Accession Numbers NM_000186.3 (variant 1) and NM_001014975.2 (variant 2). Details of the amino acid sequences encoded by CFAH can also be accessed from the UniProt database wherein the UniProt ID for human CFAH is P08603 (variant 1) and F8WDX4 (variant 2).

With reference to the paragraphs above, it is to be made clear that reference to ANXA1, ARP3, SAHH, SERPH, ARAP1, OTUB1, ATP1A1, UBA1 and CFAH includes a reference to naturally-occurring variants of these proteins (antigens). In this regard, a "variant" may exhibit an amino acid sequence (or nucleic acid sequence encoding the amino acid sequence) that is at least 80% identical, at least 90% identical, at least 95% identical, at least 98% identical, at least 99% identical, or at least 99.9% identical to the native sequence. In some embodiments, a variant of the native protein may retain native biological activity or a substantial equivalent thereof. In some embodiments, a variant may have no substantial biological activity, such as those variants which are precursors for the biologically active protein. Examples of naturally occurring variants of ARP3, SAHH, SERPH, ARAP1, OTUB1, ATP1A1, UBA1 and CFAH are described above.

In the methods of the aforementioned aspects of the invention, the presence or level of more than one autoantibody may also be detected. Detecting the presence or level of particular combinations of autoantibodies may provide greater sensitivity, specificity and predictive power than any one autoantibody alone. In this regard, the inventors have shown that by using a combination of the aforementioned autoantibodies sensitivity and specificity in identifying true positives and true negatives is maximised. For example, detecting the presence or level of a combination of an autoantibody to ANXA1, an autoantibody to ARP3, an autoantibody to SAHH, and an autoantibody to SERPH, provides the greatest sensitivity and specificity (of the combinations tested) in identifying true positives and true negatives. Furthermore, a combination of an autoantibody to ANXA1, an autoantibody to ARP3, and an autoantibody to SAHH also showed significant specificity and sensitivity. Still further, the inventors have shown that combining the data from an autoantibody to ANXA1, an autoantibody to ARP3, and an autoantibody to SAHH in a subject, with the presence or level of tumour associated antigen CA125 in the subject, also provides significant specificity and sensitivity.

Accordingly, in some embodiments of the aforementioned aspects of the invention, the presence or level of an autoantibody to ANXA1, an autoantibody to ARP3, and an autoantibody to SAHH is detected in the subject. In some embodiments, the presence or level of an autoantibody to ANXA1, an autoantibody to ARP3, an autoantibody to SAHH, and an autoantibody to SERPH is detected in the subject. In some embodiments, the presence or level of an autoantibody to ANXA1, an autoantibody to ARP3, an autoantibody to SAHH, and tumour associated antigen CA125 is detected in the subject.

As used herein, the term "subject" refers to any animal (e.g. a mammal), including, but not limited to humans, non-human primates, dogs, cats, horses, cattle, sheep, deer, pigs, rodents, and any other animal known to get ovarian cancer. Therefore, whilst information regarding the human ANXA1, ARP3, SAHH, SERPH, ARAP1, OTUB1, ATP1A1, UBA1 and CFAH antigens has been referred to above, it should be appreciated that the methods of the present invention are not limited to humans. Details of these antigens in other species, and their associated amino acid and mRNA sequences, may be readily accessed from the GenBank and UniProt databases or sequences may be identified by BLAST searching.

The present invention also enables compositions which can be used to perform any one or more of the aforementioned methods of the invention. Accordingly, in a fifth aspect the present invention provides a composition for detecting ovarian cancer in a subject, for screening for early stage ovarian cancer in a subject and/or for assessing progression of ovarian cancer in a subject, the composition including an agent that binds to, or interacts with, one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment of the fifth aspect of the invention, the agent is an antigen from which the one or more autoantibodies was derived or is an antibody specific for the one or more autoantibodies. Details regarding these agents are provided above.

In a sixth aspect, the present invention provides a kit for detecting ovarian cancer in a subject, for screening for early stage ovarian cancer in a subject, and/or for assessing progression of ovarian cancer in a subject, the kit including means for detecting the presence of one or more ovarian cancer-associated autoantibodies in the subject, wherein the one or more ovarian cancer-associated autoantibodies are selected from the group consisting of an autoantibody to ANXA1, an autoantibody to ARP3, an autoantibody to SAHH, an autoantibody to SERPH, an autoantibody to ARAP1, an autoantibody to OTUB1, an autoantibody to ATP1A1, an autoantibody to UBA1, and an autoantibody to CFAH.

In one embodiment, means for detecting the presence of one or more ovarian cancer-associated autoantibodies in the subject includes a solid support, such as a chip, sensor, a microtiter plate or a bead or resin having a capture reagent attached thereon, wherein the capture reagent binds to an autoantibody of the invention. For example, the capture reagent may be the antigen from which the autoantibody was derived, as described above. Therefore, for example, the kit can comprise mass spectrometry probes for SELDI, such as ProteinChip® arrays, or a versatile fibre-based SPR sensing device. In the case of biospecific capture reagents, the kit can comprise a solid support with a reactive surface, and a container comprising the biospecific capture reagent.

In one embodiment, the kit can also include a washing solution or instructions for making a washing solution, in which the combination of the capture reagent and the washing solution allows capture of one or more of the autoantibodies on the solid support for subsequent detection by, for example, mass spectrometry or immunological techniques (e.g. ELIZA). The kit may include more than one type of adsorbent, each present on a different solid support.

In some embodiments, such a kit can include instructions for suitable operational parameters in the form of a label or separate insert. For example, the instructions may inform a consumer about how to collect the sample to be tested, how to wash the probe or the particular autoantibody to be detected.

In some embodiments, the kit can include one or more containers with samples that represent a reference level for each autoantibody, and are therefore to be used as standards for calibration.

The present invention also enables methods and compositions for the treatment of ovarian cancer. For example, one or more of the ANXA1, ARP3, SAHH, SERPH, ARAP1, OTUB1, ATP1A1, UBA1 and CFAH antigens can be used in a therapeutic modality to immunise subjects suffering from ovarian cancer. Stimulation of an immunological response to such antigens is intended to elicit a more effective attack on cancerous cells which can thereby inhibit growth of the cells or even facilitate killing of the cancerous cells. The identification of autoantibodies to these antigens in ovarian cancer subjects provides a basis for immunotherapy of the disease. As indicated above, any part or portion of the antigen that can specifically bind to the corresponding autoantibody may be used for immunotherapy.

In some embodiments, one or more antibodies equivalent to one or more autoantibodies of the present invention can be used in a therapeutic modality. In this instance, each antibody should possess immunoreaction characteristics of the equivalent autoantibody. As described above, an antibody fragment may also be used in such a therapeutic modality and use of the term "antibody" in the context of this aspect of the invention is taken to include an antibody fragment. Antibodies for therapeutic applications, or any other application referred to herein, can be produced according to well-established techniques in the art, including those described above.

Each antibody, once administered, will recognise the corresponding antigen present on cancerous cells in the subject to be treated. Accordingly, each antibody can be combined with a variety of radionuclides and/or cytotoxic drugs to kill the cancerous cells. Examples of radiologic groups that may be used include alpha-emitting and beta-emitting radionuclides such as I-131, Yt-99, Cu-67, Au-198, P-32, and other cytotoxic radionuclides. The radionuclides can be conjugated to the carrier antibody using methods that are familiar to those skilled in the art. For example, the carrier antibody can be iodinated using the chloramine-T method to label the antibody with 1-125 or 1-131. Other radionuclides may be attached to the carrier antibody by chelation with benzyl EDTA or DPTA conjugation procedures. For cancer treatment a high dosage of radioactivity is typically employed. The labelled carrier antibody is then injected into the affected subject where it will localize in the necrotic regions within the tumour. From there the radiation will penetrate into the surrounding tumour where it will have a cytotoxic effect upon the cancerous cells.

Examples of suitable cytotoxic drugs that can be combined with the therapeutic antibody include folate inhibitors, pyrimidine analogs, purine analogs, alkylating agents and antibiotics. Specific examples include acivicin, aclarubicin, acodazole, adriamycin, ametantrone, aminoglutethimide, anthramycin, asparaginase, azacitidine, azetepa, bisantrene, bleomycin, busulfan, cactinomycin, calusterone, caracemide, carboplatin, carmustine, carubicin, chlorambucil, cisplatin, cyclophosphamide, cytarabine, dacarbazine, dactinomycin, daunorubicin, dezaguanine, diaziquone, doxorubicin, epipropidine, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin. Also included are the toxins such as ricin and diptheria toxin. All of these compounds can be conjugated to the carrier antibody using methods that are familiar to those skilled in the art. For example, many carboxylic acid-containing compounds such as methotrexate can be conjugated to immunoglobulins through an active ester intermediate by reacting the compound with N-hydroxysuccinimide and dicyclohexylcarbodiimide; amino sugar containing drugs such as adriamycin and daunomycin may be covalently bound to antibodies by periodate oxidation of the drug, followed by linking of the oxidized drug to the immunoglobulin and subsequent reduction of the product with sodium borohydride. The methods of conjugating any particular drug to the carrier antibody will vary depending upon the nature of the drug. However, these are performed according to conventional laboratory methods and are considered to be within the scope of this invention. The labelled carrier antibody is then administered to the affected subject where it will localize in the necrotic regions within the tumour. From there the drug will diffuse into the surrounding tissues where it will have a cytotoxic effect upon the cancerous cells.

In some embodiments, the treatment may include a combination therapy where one or more of the ANXA1, ARP3, SAHH, SERPH, ARAP1, OTUB1, ATP1A1, UBA1 and CFAH antigens can be combined with one or more of the antibodies equivalent to these antigens.

In light of the therapeutic applications described above, in a further aspect, the present invention provides a pharmaceutical composition for treating or preventing ovarian cancer in a subject, the composition including an effective amount of one or more of the ANXA1, ARP3, SAHH, SERPH, ARAP1, OTUB1, ATP1A1, UBA1 and CFAH antigens, and/or an effective amount of one or more antibodies to one or more of these antigens (as described above).

The pharmaceutical composition may also include the use of one or more pharmaceutically acceptable additives, including pharmaceutically acceptable salts, amino acids, polypeptides, polymers, solvents, buffers, excipients and bulking agents, taking into consideration the particular physical and chemical characteristics of the agent(s) to be administered. The preparation of such pharmaceutical compositions is known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa.

For example, the antigens and/or antibodies can be prepared into a variety of pharmaceutical compositions in the form of, for example, an aqueous solution, an oily preparation, a fatty emulsion, an emulsion, a gel, etc., and these preparations can be administered as intramuscular or subcutaneous injection or as injection to an organ (e.g. ovary), or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the antigens and/or antibodies may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, a-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The pharmaceutical composition may also contain a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the agent(s) being administered.

For these purposes, the composition may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

When administered orally, the pharmaceutical composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or moulding the pharmaceutical composition optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the pharmaceutical composition in the various embodiments of the present invention may also utilise controlled release technology. The composition may also be administered as a sustained-release pharmaceutical. To further increase the sustained release effect, the pharmaceutical composition may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the pharmaceutical composition may be incorporated into a hydrophobic polymer matrix for controlled release over a period of days. The composition may then be moulded into a solid implant, or externally applied patch, suitable for providing efficacious concentrations of the active agent(s) over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time release characteristics and release kinetics. The pharmaceutical composition may then be moulded into a solid implant suitable for providing efficacious concentrations of the active agent(s) over a prolonged period of time without the need for frequent re-dosing. The pharmaceutical composition can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

For topical administration, the composition of the present invention may be in the form of a solution, spray, lotion, cream (for example a non-ionic cream), gel, paste or ointment. Alternatively, the composition may be delivered via a liposome, nanosome, or nutri-diffuser vehicle.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are mono-, di- and triglycerides of fatty acids or fatty alcohols with soaps, alkyl sulphates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste contains a large proportion (20-50%) of dispersed solids in a fatty or aqueous vehicle. An ointment tends not to evaporate or be absorbed when rubbed onto the skin.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension semisolid dosage form for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminium silicates, xanthan gum, colloidal silica, and aluminium or zinc soaps.

The composition for topical administration may further include drying agents, anti-foaming agents; buffers, neutralizing agents, agents to adjust pH; colouring agents and decolouring agents; emollients; emulsifying agents, emulsion stabilizers and viscosity builders; humectants; odorants; preservatives, antioxidants, and chemical stabilizers; solvents; and thickening, stiffening, and suspending agents, and a balance of water or solvent.

The autoantibodies of the present invention can also be used for the purposes of imaging a tumour or cancerous cell in a subject. In this regard, the autoantibodies can be combined with a wide variety of tumor imaging agents. These include radionuclides such as Tc-99m, I-123, I-125, In-111, In-113m, Ga-67, or other gamma-emitters. The autoantibody can also be iodinated using the chloramine-T method to label the protein with I-125 or I-131. Other radionuclides may be attached to the carrier autoantibody by chelation with benzyl EDTA or DPTA conjugation procedures as referred to above. The radionuclide labelled carrier autoantibodies are then injected into the affected subject where they will come into contact with the tumour tissue or cancerous cells. The labelled autoantibodies will bind to the corresponding tumour associated antigen present in the tumour or cancerous cells and the radioactivity will become localized within the tumourigenic regions. In contrast, the labelled autoantibodies will not recognise normal tissues and cells which do not express the antigen. The quantity of radioactivity in different tissue locations is measured using gamma ray scanning or tissue sampling techniques.

The term "about" as used in the specification means approximately or nearly and in the context of a numerical value or range set forth herein is meant to encompass variations of +/−10% or less, +/−5% or less, +/−1% or less, or +/−0.1% or less of and from the numerical value or range recited or claimed.

Reference is made to standard textbooks of molecular biology that contain methods for carrying out basic techniques encompassed by the present invention. See, for example, Green MR and Sambrook J, Molecular Cloning: A Laboratory Manual (4th edition), Cold Spring Harbor Laboratory Press, 2012.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is further illustrated in the following examples. The examples are for the purpose of describing particular embodiments only and are not intended to be limiting with respect to the above description.

Example 1

Identification of Ovarian Cancer Autoantibodies

The inventors have used a sophisticated immunoproteomics technology to identify autoantibodies that are produced by subjects with the earliest stages of ovarian cancer. Autoantibodies raised against tumour-associated antigens represent a novel way to detect early stage ovarian cancer and improve the survival of patients. Autoantibodies are ideal candidates for biomarker validation and screening as they are detectable in the blood of patients at early stages of cancer development due to signal amplification via the humoral immune response. Furthermore, circulating autoantibodies are metabolically stable, which allows for their reliable detection and facilitates their use in the development of diagnostics. Finally, autoantibodies are present in the sera of patients, an accessible biological material, and can therefore be analysed through well-established techniques as described in detail above.

Materials and Methods

This study explored the presence of autoantibodies to tumour associated antigens in the sera and plasma of patients diagnosed with serous ovarian cancer. The discovery phase utilised an immunoproteomic strategy outlined in FIG. 1 and described in further detail below. Immuno-captured autoantigens, derived from ovarian cancer tissue, were eluted from paired patient specific and control immunoaffinity columns. Relative quantification of eluted proteins was then performed using isotope coded protein label (ICPL) technology. Subsequent verification of identified autoantibody biomarker candidates was performed using protein microarray. Those autoantibody candidates that best discriminated between early ovarian cancer versus healthy and benign disease represented ideal biomarkers for ovarian cancer detection.

Clinical Samples

Ethics approval was granted by the local Research Ethics Committee (Royal Adelaide Hospital (RAH), Adelaide, Australia) prior to commencement of the study and signed consent was provided by patients undergoing surgery for gynaecological disease. Pre-therapeutic serum and tissue specimens collected from the primary ovarian site during surgery were stored at −80° C. Biospecimens acquired from other institutions or biobanks had patient consent and ethics approval according to the ethics regulation of the participating centre. Sample exclusion criteria included those individuals with a personal history of cancer and secondary malignancies. Where possible control samples were matched based on age, menopausal status and collection centre/repository.

The discovery cohort included tissue and serum from 12 serous ovarian cancer patients as well as serum from 10 patients with benign gynaecological disease and 10 healthy individuals. Demographic information for the discovery cohort is shown in Table 1 below.

TABLE 1

| Demographic | Characteristic | Serous ovarian cancer (n = 12) | Healthy (n = 10) | Benign (n = 10) |
|---|---|---|---|---|
| Age | Mean ± SD | 54.3 ± 10.5 | 49.8 ± 8.0 | 58.9 ± 12.5 |
|  | range | 37-75 | 42-70 | 44-84 |
| Menopausal status | Pre | 5 | 6 | 3 |
|  | Post | 7 | 4 | 7 |
| FIGO stage | III | 12 |  |  |
| Institute/Biobank | RAH | 12 | 10 | 10 |

For verification of candidate autoantibody biomarkers an independent sample cohort (n=98) was used as shown in Table 2 below. Of those samples, 11 stage III serous ovarian cancer cases and 5 controls were previously analysed as part of the discovery cohort. Plasma from 10 stage I/II serous ovarian cancer patients, sourced from Prince Henry's Institute (PHI) of Medical Research, VIC, Australia, were also examined.

TABLE 2

| Demographic | Characteristic | Serous ovarian cancer (n = 38) | Healthy (n = 30) | Benign (n = 30) |
|---|---|---|---|---|
| Age | Mean ± SD | 60.4 ± 12.6 | 55.8 ± 11.7 | 56.4 ± 12.4 |
|  | range | 37-86 | 42-61 | 25-86 |

TABLE 2-continued

| Demographic | Character-istic | Serous ovarian cancer (n = 38) | Healthy (n = 30) | Benign (n = 30) |
|---|---|---|---|---|
| Menopausal status | Pre | 11 | 11 | 9 |
| | Post | 27 | 19 | 21 |
| FIGO stage | I | 10 | | |
| | II | 8 | | |
| | III | 20 | | |
| Institute/Biobank | RAH | 28 | 30 | 30 |
| | PHI | 10 | | |

Tissue Protein Extraction and Antibody Purification

Ovarian tissue (approximately 1.2 g) was sliced from the tumour mass and snapped frozen in liquid nitrogen. Mechanical homogenisation was performed using a mortar and pestle and proteins extracted into a native extraction buffer (150 mg/mL) containing 1×TBS pH 7.5, 1% Triton X-100, 1% protease inhibitor cocktail (Sigma-Aldrich) and 1% Pefabloc SC PLUS protector solution (Roche Applied Science). The homogenate was incubated at 4° C. for 2 hours and subjected to ultracentrifugation (100,000×g, 2 hrs, 15° C.) to remove cellular debris. Protein concentration was determined using the EZQ® protein quantitation assay (Invitrogen™, CA, USA).

Immunoglobulin G was purified from serum using a 1 mL Pierce® Chromatography Cartridge Melon™ Gel (Pierce Biotechnology, IL, USA) following the manufacturer's instructions. Briefly, serum (0.5 mL) was diluted by factor of 10 in Melon™ Gel purification buffer (proprietary, Pierce Biotechnology, IL, USA) and applied to the chromatography cartridge at 0.5 mL/min using a syringe pump. For the purification of pooled healthy and benign sera (10 mL) a 5 mL Pierce® Chromatography Cartridge Melon™ Gel (Pierce Biotechnology, IL, USA) was employed. Prior to antibody purification pooled sera was dialyzed in Melon™ Gel purification buffer (Pierce Biotechnology, IL, USA) using CelluSep® Regenerated Cellulose Tubular Membrane (MWCO 12-14 kDa, Membrane Filtration Products Inc., Seguin, Texas, USA). Dialysis was performed in 1 litre of buffer at 4° C. for 1 hour with stirring. The buffer was then exchanged and dialysis continued for 2 hours. Finally, dialysis was performed overnight in fresh buffer and IgG purified from dialysed serum as described above following manufacturer's instructions.

Immunoaffinity Chromatography

Purified IgG was buffer exchanged into 0.02 M HEPES coupling buffer (pH 6.8) using a Vivaspin500 device (10 kDa MWCO, Sartorius Stedium Biotech) and protein concentration determined using the EZQ® protein quantitation assay (Invitrogen™, CA, USA). IgG (4 mg) was coupled to 0.6 mL Affi-Gel 10 Activated Affinity Media (Bio-Rad Laboratories Inc., CA, USA) overnight at 4° C. with gentle agitation. The reaction was stopped by the addition of 200 mM glycine (pH 6.8) for 1 hour at room temperature with gentle agitation. The Affii-Gel immobilised IgG slurry was poured into a Poly-Prep® chromatography column (Bio-Rad). The column was washed with 4 column volumes of PBST (0.1% Tween-20) and 1 column volume of TBST (0.01% Tween-20).

Pre-cleared tissue protein lysate (27 mg) was applied to the immunoaffinity column and allowed to incubate overnight at 4° C. with gentle agitation. Prior to auto-antigen elution the column was washed 5 times with 9 mL of PBS 0.1% Tween-20 for 5 minutes at 4° C. with gentle agitation. Elution of immuno-captured auto-antigens was performed in one step using 0.5 mL TUC4 buffer (7 M urea, 2 M thiourea, 4% CHAPS, 34 mM Tris) for 45 minutes at room temperature. Eluted auto-antigens were buffer exchanged into 6 M guanidine HCl, pH 8.5 (pH 6.8) using a Vivaspin500 device (10 kDa MWCO, Sartorius Stedium Biotech) and protein concentration determined using the EZQ® protein quantitation assay (Invitrogen™, CA, USA).

Isotope Coded Protein Labelling (ICPL)

ICPL labelling was performed using the duplex ICPL-kit (Serva Electrophoresis, Heidelberg, Germany) according to the manufacturer's instructions and as described in Lottspeich F and Kellermann J, 2011, Methods in Molecular Biology, 753: 55-64. Briefly, each sample (15 µg) was adjusted to 2.5 µg/µl by the addition of 6 M guanidine HCl, pH 8.5. Reduction and alkylation of disulfide bonds was performed with 0.2 M tris(2-carboxyethyl)phosphine and 0.4 mM iodoacetamide, respectively. Labelling of lysine residues and the N-terminus of proteins was performed with either the light ($^{12}$C-nicotinoyloxysuccinimide) or the heavy ($^{13}$C-nicotinoyloxysuccinimide) ICPL for 2 hours at room temperature. Upon completion, excess reagent was quenched with 6 M hydroxylamine and paired light/heavy labelled samples were combined. Combined samples were concentrated by acetone-precipitation, dissolved in 1×LDS sample buffer (Invitrogen) and pre-fractionated by 1D SDS-PAGE. Upon protein visualization using Coomasie blue G-250, 20 gel bands were excised and subjected to in-gel tryptic digestion as described in Condina M R et al., 2009, Proteomics 9: 3047-3057. Proteolytic peptides were then extracted from the gel by sequential incubation in the following solutions: 1% FA (v/v), ACN/H2O/FA, 50/50/1 (v/v/v) and 100% ACN. Pooled peptide extracts were concentrated to a final volume of 1 µl by vacuum centrifugation and reconstituted to 10 µl in ACN/H2O/FA, 3/97/1 (v/v/v).

Nano-LC-MS/MS

Nano-LC-MS/MS analysis was performed on an LTQ Orbitrap XL mass spectrometer (Thermo Fisher Scientific, Bremen, Germany) coupled to an Ultimate 3000 rapid separation liquid chromatography (RSLC) system (Thermo Fisher Scientific, Bremen, Germany). Briefly, peptides were pre-concentrated on a reverse phase trapping column (Acclaim PepMap 100 nano trap, 100 µm id, length 2 cm, C18 particle size 3 µm, pore size 100 Å, Thermo Fisher Scientific) and subsequently separated on an analytical capillary column (100 µm id, length 15 cm, C18 particle size 5 µm, pore size 100 Å, Nikkyo Technos Co., Ltd) using a binary gradient (solvent A: 0.1% FA, 2% ACN, solvent B: 0.1% FA, 80% ACN) at a flow rate of 300 nL/min. Peptides were analyzed using a 60 min elution program: 4% B for 10 min; linear gradient 4 to 55% of B in 40 min, maintained at 90% of B for 10 min; re-equilibration of the columns with 4% B for another 10 minutes. Full MS survey scans from m/z 300 to 2000 were acquired on the LTQ-Orbitrap XL mass spectrometer at a resolution of 60,000 (full width at half maximum) at m/z 400. Orbitrap automatic gain control (AGC) target ion count was set to $1×10^6$ for MS with maximum fill time of 500 ms. The six most intense peaks were subjected to MS/MS in the ion trap with the AGC value set to $1×10^4$ with maximum fill time of 100 ms. CID spectra were acquired with a normalized collision energy of 35%; dynamic exclusion time of 30 s; precursor ion isolation width of m/z 3.0; spectra were recorded in profile mode; activation time of 30 ms. Singly charged and charge-unassigned precursor ions were excluded.

Protein Identification and Relative Quantification

Relative protein quantification was obtained using ICPL_ESIQuant software (v2.0) as described in Brunner A et al., 2010, Proteomics, 10: 315-326; Achim Brunner J K et al., 2012, *Proteomics Bioinform.*, 5: 279-282; and Brunner A et al., 2013, *Biochimica et Biophysica acta*, doi:10.1016/j.bbapap.2013.02.019. Here, RAW data files were converted to the open mzXML format (Pedrioli P G et al., 2004, *Nat. Biotechnol.*, 22: 1459-1466) using MSConvert (release 3.0.4001)(Kessner D et al., 2008, *Bioinformatics*, 24: 2534-2536) and analyzed using the following parameters: 20 ppm label delta accuracy, 0.02 Da isotopic pattern accuracy, charge state range from +2 to +5, compound size and coelution count ≥2. All other quantification parameters were kept at the recommended default settings. Proteome Discoverer v1.3 software (Thermo Fisher Scientific) was used to search MS/MS spectra against the UniprotKB/Swiss-Prot database (release 2011_08, mammalian taxonomy, 65451 sequence entries) using the Mascot algorithm (Mascot server v2.3.02, Matrix Science). Searchers were performed using the following parameters: trypsin digestion with two missed cleavages allowed, ±0.01 Da precursor tolerance, 0.5 Da fragment-ion tolerance, fixed carbamidomethylation of cysteine and variable oxidation of methionine. Labeling of the N-terminus or lysine residues by the light (ICPL_0, monoisotopic mass 105.02 Da) or heavy (ICPL_6, monoisotopic mass 111.04) ICPL reagents was set as a variable modification. Protein lists for each ICPL duplex analysis (corresponding to the 20 bands) were compiled. Identified proteins were considered deregulated based upon the following criteria: protein ratio 0.5≥x≥1.5 fold (>35D), labelled peptides per protein 2, protein coefficient of variance≤15%.

Gene Ontology (GO) analysis was performed using the Universal Protein Resource Knowledgebase (UniProtKB, UniProt Consortium, uniprot.org) to investigate the "cellular component" and "biological process" of disregulated auto-antigens. Biological and disease networks were investigated using IGENUITY Pathway Analysis (IPA) software (Ingenuity® Systems, ingenuity.com). Autoantibody candidates were selected for verification based upon dis-regulation in multiple patients, GO annotations and commercial availability of recombinant auto-antigen.

Protein Microarray

Protein microarrays were generated and analyzed by Arrayit® Corporation (Sunnyvale, CA, USA). Briefly, recombinant auto-antigens (OriGene Technologies/Abnova) were printed onto SuperEpoxy 2 glass microarray substrate slides, at a final concentration of 0.3 µg/µl, using a NanoPrint™ protein microarray spotter. Array spots were approximately 50 µm in diameter with a 200 µm horizontal and vertical pitch. Auto-antigens were arrayed in triplicate resulting in an array of 3,600 spots (150 spots per microarray) across 5 arrays for a total of 17,550 spots. Blocking was performed for 1 hr using Blocklt™ Plus and serum (1:100 dilution in Reaction Buffer Plus) applied to each protein microarray for 1 hr at room temperature. Autoantibody binding was detected using a Cy5-conjugated secondary antibody (Alexa Fluor® 647-AffiniPure Goat Anti-Human IgG (H+L) (JacksonImmuno Research). Fluorescence detection was performed using an InnoScan 710 microarray scanner at a wavelength of 635 nm, 3 µm resolution, 10 laser power and 100 PMT detection gain. Image quantification to yield spot intensity data was performed using Mapix software V4.6.2.

Mean spot pixel intensity data with local feature background subtraction were used to calculate an average from each triplicate. Variance stabilization and normalization (vsn)(Huber W et al., 2002, *Bioinformatics* 18(Suppl 1): S96-S104; and Sundaresh S et al., 2006, *Bioinformatics* 22: 1760-1766) as well as analysis of variance (ANOVA) and post-hoc Tukey's 'Honest Significant Difference' (HSD) tests were performed using R (A language and environment for statistical computing, V2.15.2). Receiver-operating characteristic (ROC) analysis was performed using GraphPad Prism (V6.0b) to estimate the sensitivity and specificity of the candidate autoantibody biomarkers.

Results

The immunoproteomic approach for identifying ovarian cancer autoantibodies is shown in FIG. 1 with details of the steps described above. This led to the identification of nine autoantibody candidates that were subsequently validated for specificity and sensitivity in detecting ovarian cancer subjects. The candidates included autoantibodies to ANXA1, ARP3, SAHH, SERPH, ARAP1, OTUB1, AT1A1, UBA1 and CFAH. Information regarding these proteins is provided in the detailed description section of the specification. A summary of the ICPL quantification parameters for the nine autoantibody candidates is shown in Table 3.

Representative protein microarrays demonstrating differential regulation of two of the autoantibody targets (named Autoantibody A and Autoantibody B) is shown in FIG. 2. As can be seen from FIGS. 2E and 2F, the autoantibodies are significantly upregulated in stage I cancer samples and stage III cancer samples compared to healthy and benign samples where there is little or no autoantibody present.

Figure 3A:
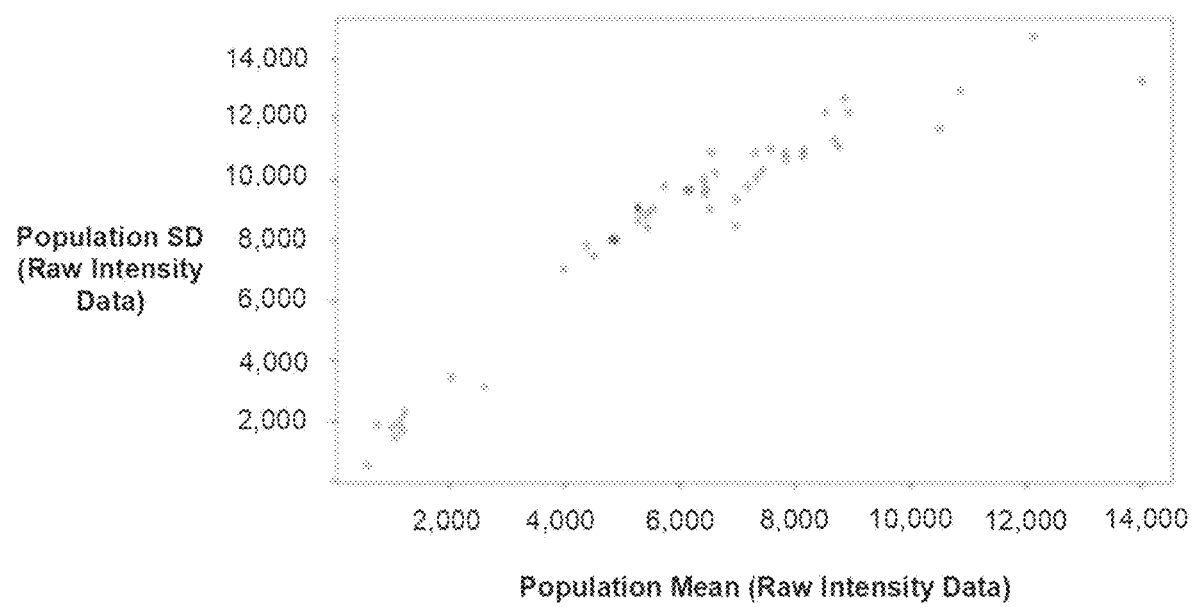
FIGS. 3A-3D—Data plots of raw and transformed protein microarray data.

A variance-mean dependence exists for intensity data acquired by DNA or protein microarray (Huber W et al., 2002, *Bioinformatics* 18(Suppl 1): S96-S104; and Sundaresh S et al., 2006, *Bioinformatics* 22: 1760-1766). Analysis of the average intensity and standard deviation for a particular antigen across all 98 samples showed this dependence (FIG. 3A). As expected, the standard deviation increases proportionally with the increase in intensity (r=0.94). Additionally, a quantile-quantile plot (q-q plot) of the averaged intensity of replicate antigens shows that the data is not normally distributed.

TABLE 3

| Protein Name | Short Name | Accession* | Patient | Multiplet Count | Protein Ratio | STDEV | CV (%) | Mascot Score (Sum) |
|---|---|---|---|---|---|---|---|---|
| Actin-related protein 3 | ARP3 | P61158 | P363 | 1 | 1.73 | 0 | 0 | 161.64 |
|  |  |  | P376 | 1 | 1.99 | 0 | 0 | 109.93 |
|  |  |  | P385 | 2 | 1.545 | 0.007071068 | 0 | 235.92 |
| Adenosylhomocysteinase | SAHH | P23526 | P56 | 2 | 1.85 | 0.028284271 | 2 | 161.63 |
|  |  |  | P385 | 4 | 1.455 | 0.085780728 | 6 | 243.25 |
| Annexin A1 | ANXA1 | P04083 | P363 | 8 | 1.49 | 0.205461154 | 14 | 407.37 |
|  |  |  | P467 | 9 | 1.54 | 0.139258239 | 9 | 674.79 |
|  |  |  | P544 | 10 | 1.55 | 0.206303444 | 13 | 597.4 |
| Serpin H1 | SERPH | P50454 | P363 | 1 | 1.63 | 0 | 0 | 41.65 |
|  |  |  | P385 | 1 | 1.44 | 0 | 0 | 35.45 |
|  |  |  | P467 | 1 | 1.66 | 0 | 0 | 89.55 |

TABLE 3-continued

| Protein Name | Short Name | Accession* | Patient | Multiplet Count | Protein Ratio | STDEV | CV (%) | Mascot Score (Sum) |
|---|---|---|---|---|---|---|---|---|
| Arf-GAP with Rho-GAP domain | ARAP1 | Q96P48 | P363 | 1 | 1.68 | 0 | 0 | 100.63 |
| | | | P363 | 1 | 1.79 | 0 | 0 | 117.94 |
| | | | P544 | 1 | 2.34 | 0 | 0 | 107.33 |
| Ubiquitin thioesterase | OTUB1 | Q96FW1 | P8 | 1 | 1.62 | 0 | 0 | 116.36 |
| | | | P363 | 1 | 1.71 | 0 | 0 | 183.82 |
| | | | P385 | 1 | 1.69 | 0 | 0 | 105.65 |
| | | | P467 | 1 | 1.47 | 0 | 0 | 124.06 |
| Sodium/potassium-transporting ATPase subunit alpha-1 | ATP1A1 | P05023 | P56 | 1 | 2.22 | 0 | 0 | 101.86 |
| | | | P363 | 1 | 1.77 | 0 | 0 | 78.09 |
| | | | P363 | 1 | 2.02 | 0 | 0 | 171.9 |
| | | | P467 | 2 | 1.54 | 0.028284271 | 2 | 171.25 |
| | | | P467 | 1 | 1.7 | 0 | 0 | 65.15 |
| | | | P467 | 1 | 1.53 | 0 | 0 | 66.91 |
| | | | P544 | 4 | 1.89 | 0.110151411 | 6 | 210.04 |
| | | | P544 | 2 | 1.905 | 0.091923882 | 5 | 102.73 |
| | | | P544 | 3 | 2.02 | 0.227156334 | 11 | 150.65 |
| Ubiquitin-like modifier-activating enzyme 1 | UBA1 | P22314 | P56 | 1 | 2.85 | 0 | 0 | 152.15 |
| | | | P281 | 1 | 1.54 | 0 | 0 | 74.21 |
| | | | P363 | 1 | 2.59 | 0 | 0 | 281.89 |
| | | | P376 | 1 | 2.45 | 0 | 0 | 140.86 |
| | | | P467 | 2 | 1.55 | 0.169705627 | 11 | 252.05 |
| | | | P544 | 2 | 2.455 | 0.728319985 | 30 | 152.66 |
| | | | P544 | 1 | 1.93 | 0 | 0 | 241.41 |
| Complement factor H | CFAH | P08603 | P363 | 3 | 5.02 | 0.33126022 | 7 | 237.01 |
| | | | P544 | 3 | 2.39 | 0.355011737 | 15 | 282.54 |

Note:
*Protein accession number from the Universal Protein Resource Knowledgebase (UniProtKB, UniProt Consortium, uniprot.org)

Figure 3B:
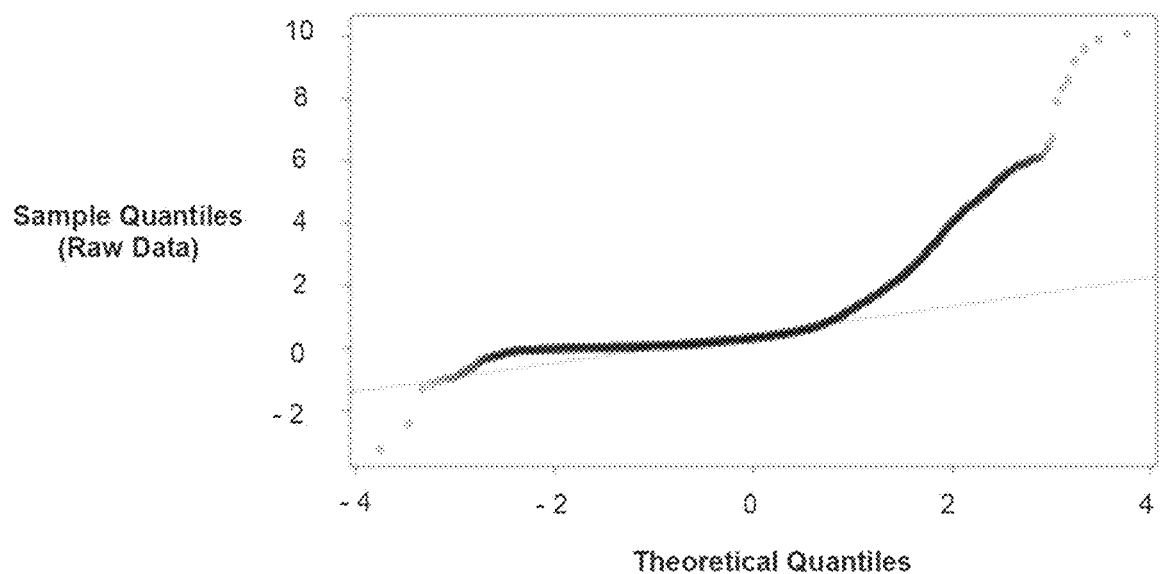
Figure 3C:
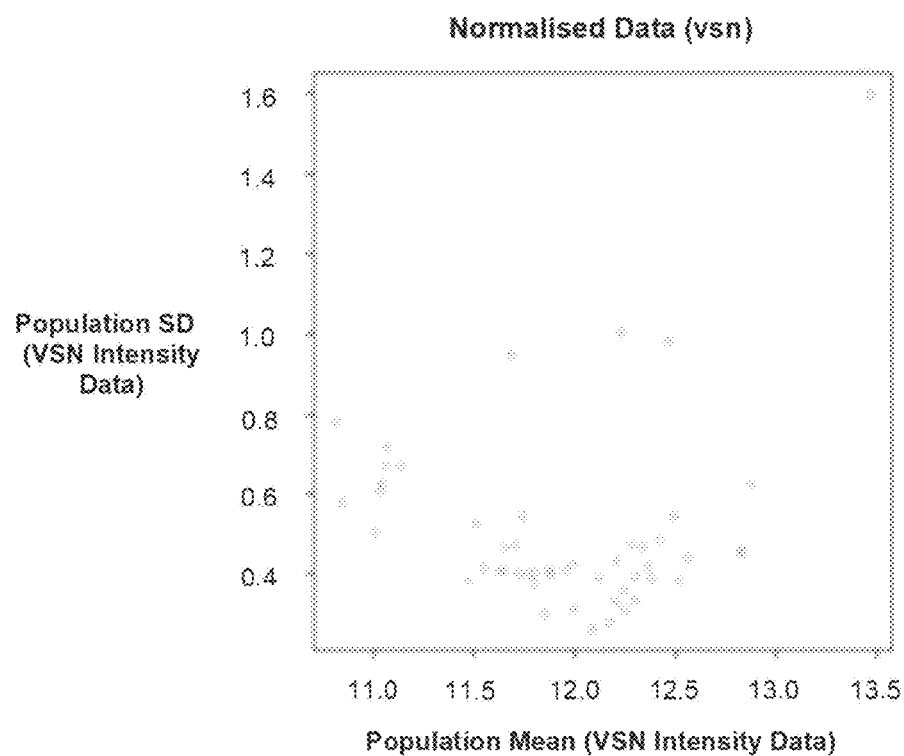
Figure 3D:
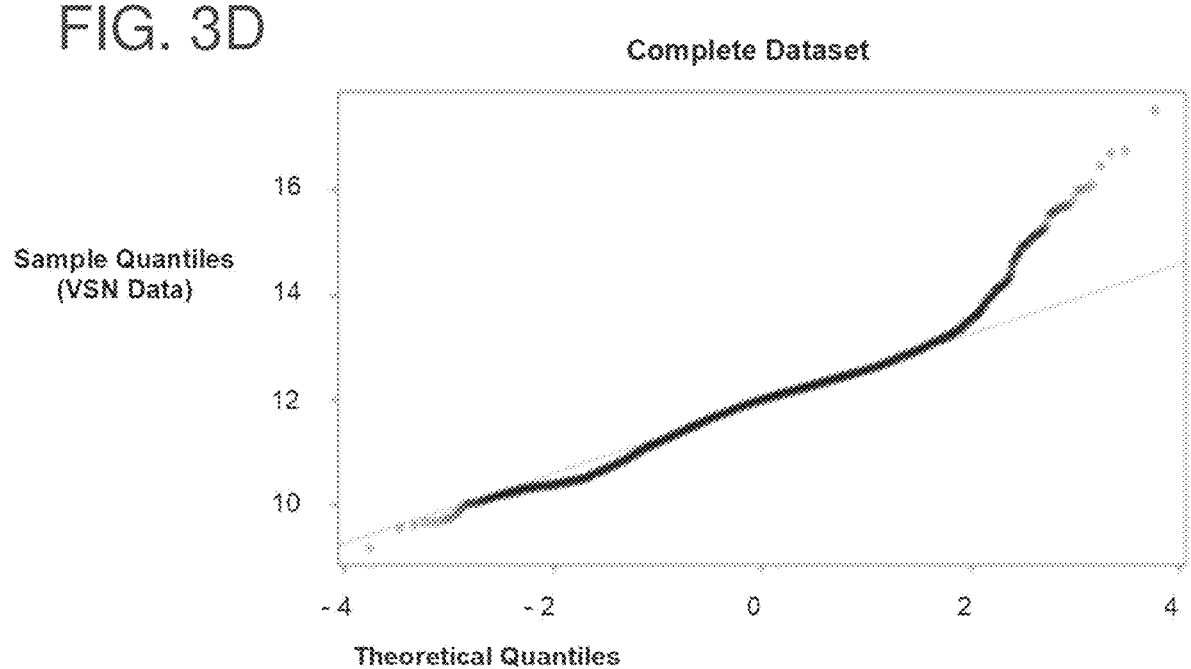
Figure 4A:
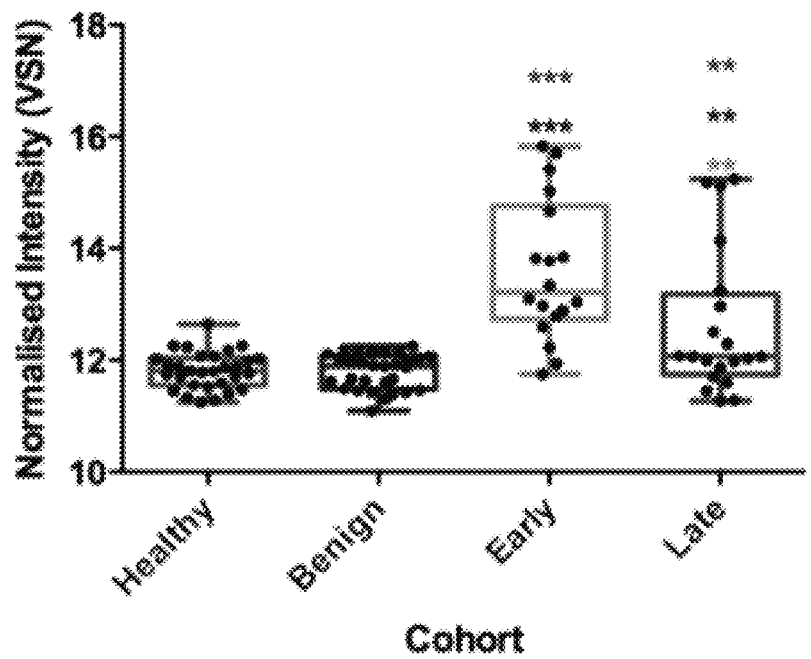
FIGS. 4A-4I— Graphs showing the regulation pattern of the selected nine autoantibodies in early and late stage ovarian disease compared to health individuals and patients with benign gynaecological disease.
Figure 4B:
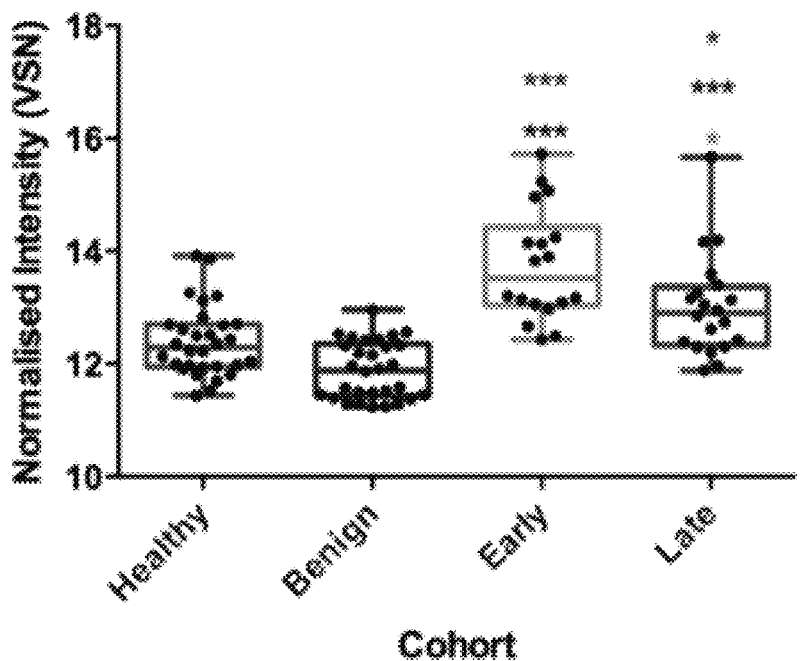
Figure 4C:
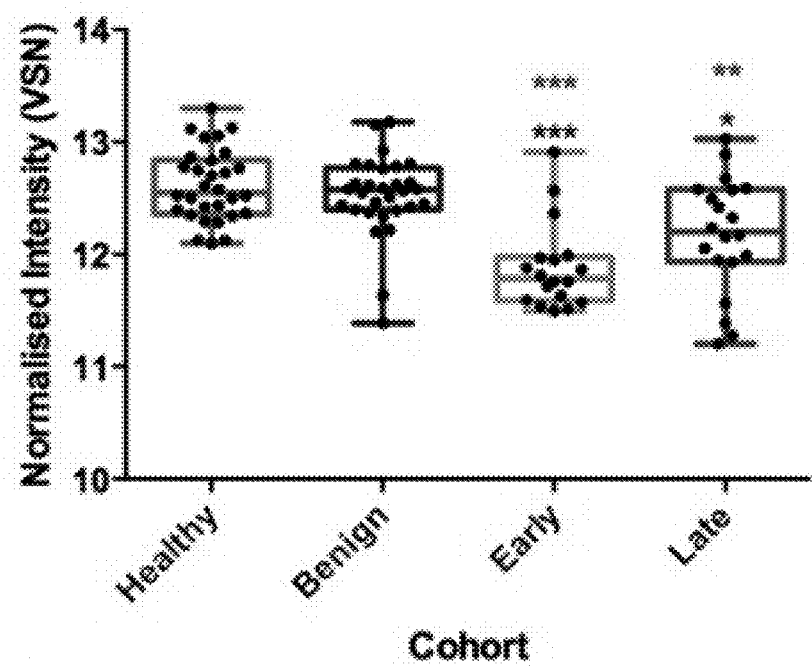
Figure 4D:
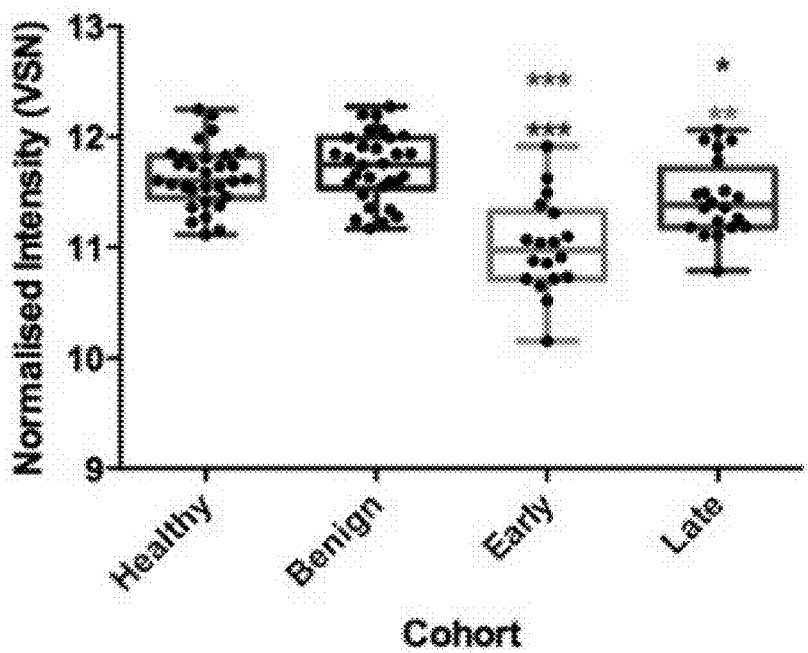
Figure 4E:
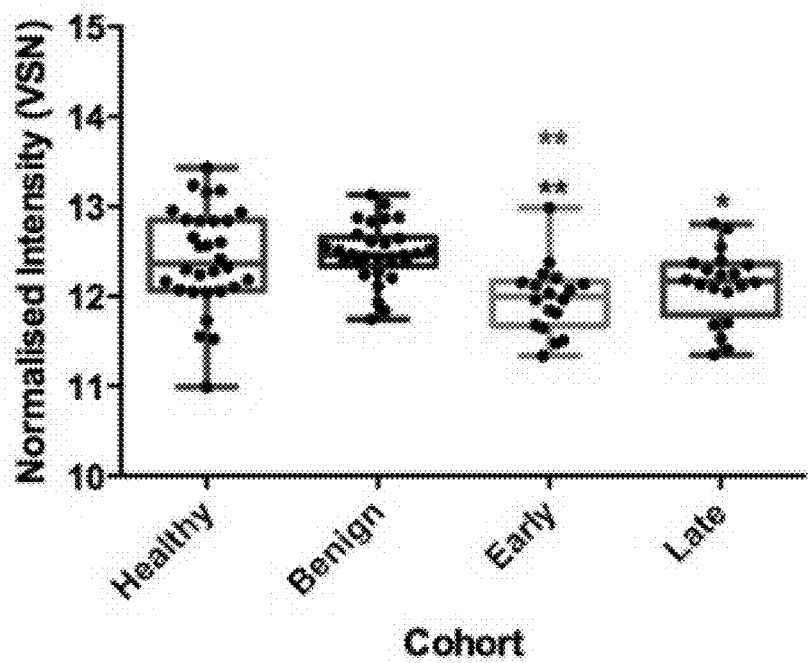
Figure 4F:
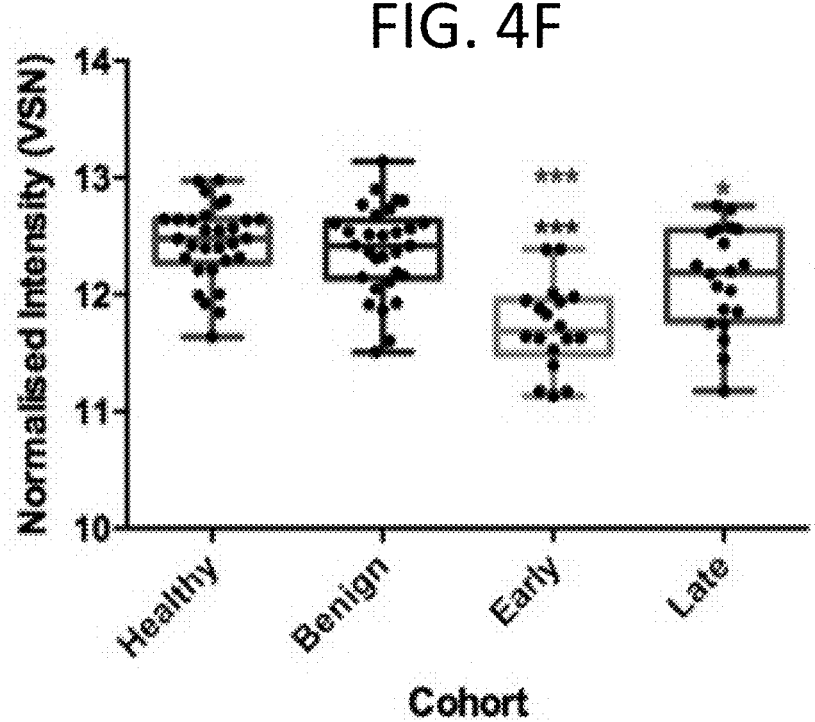
Figure 4G:
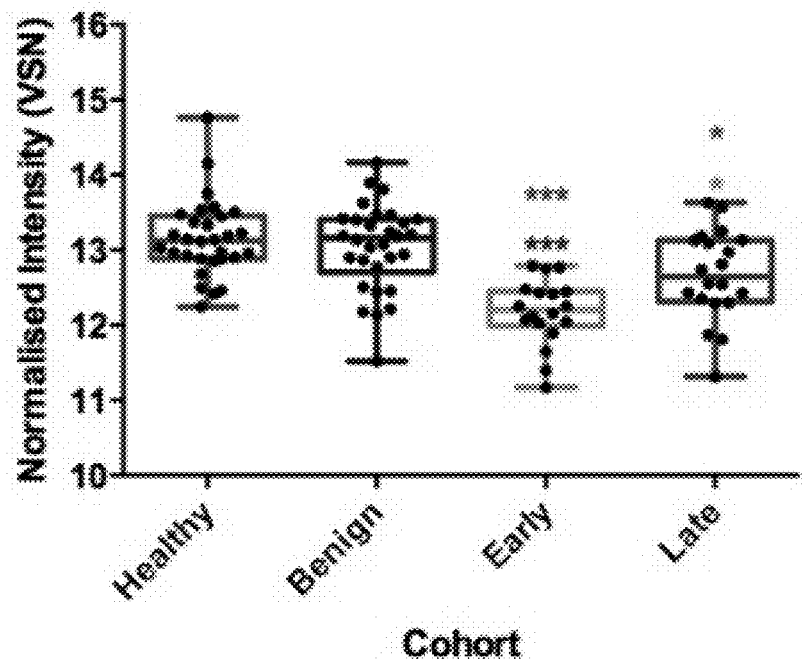
Figure 4H:
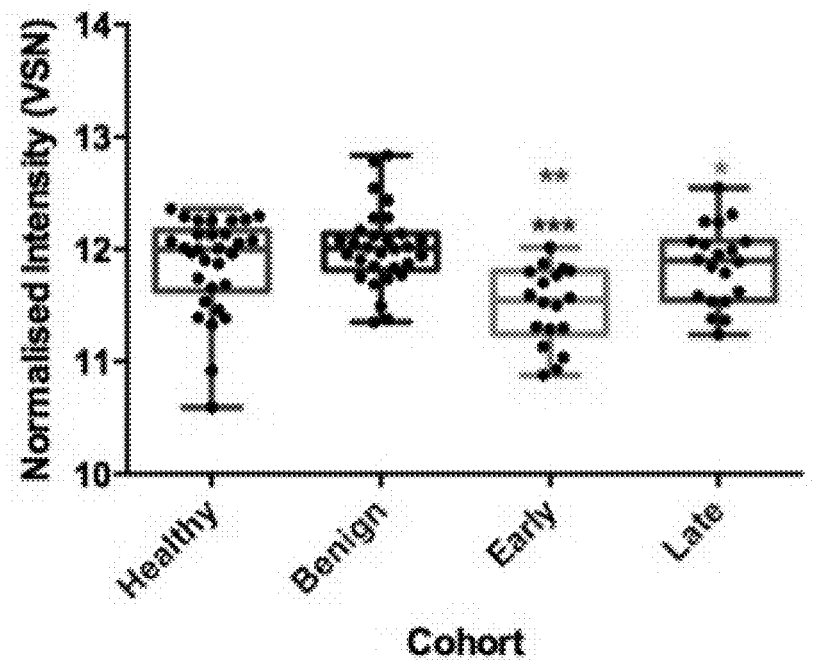
Figure 4I:
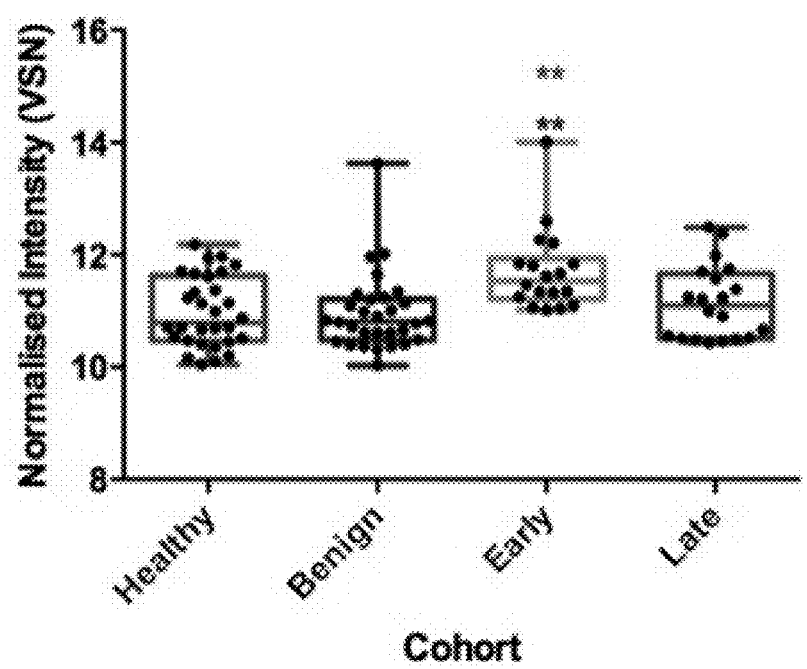
Figure 5A:
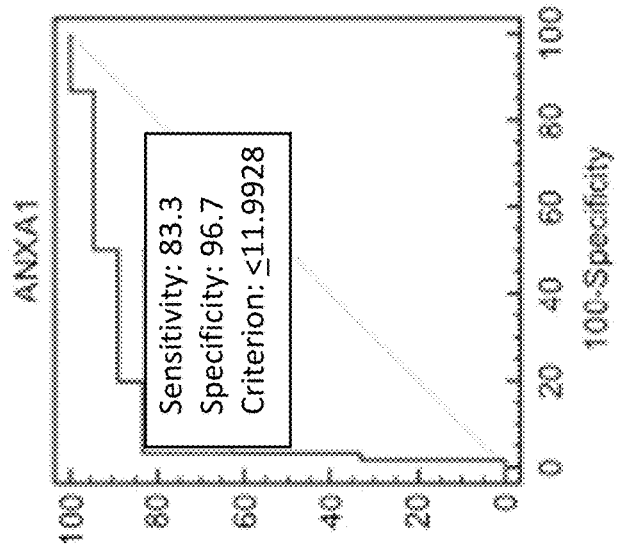
Figure 5B:
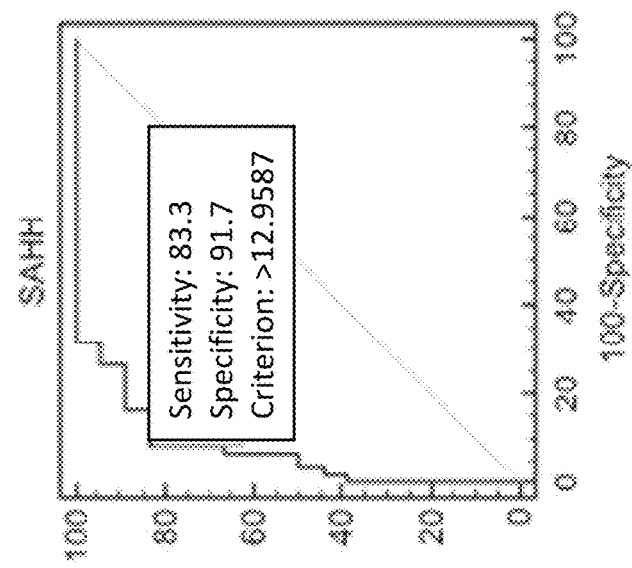
Figure 5C:
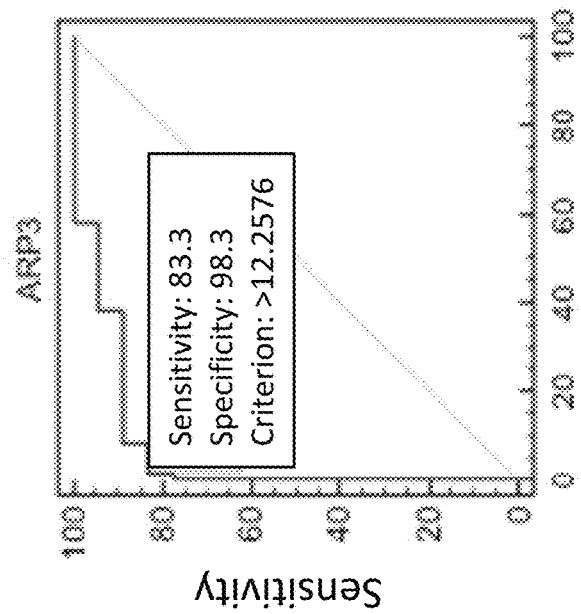
Figure 5G:
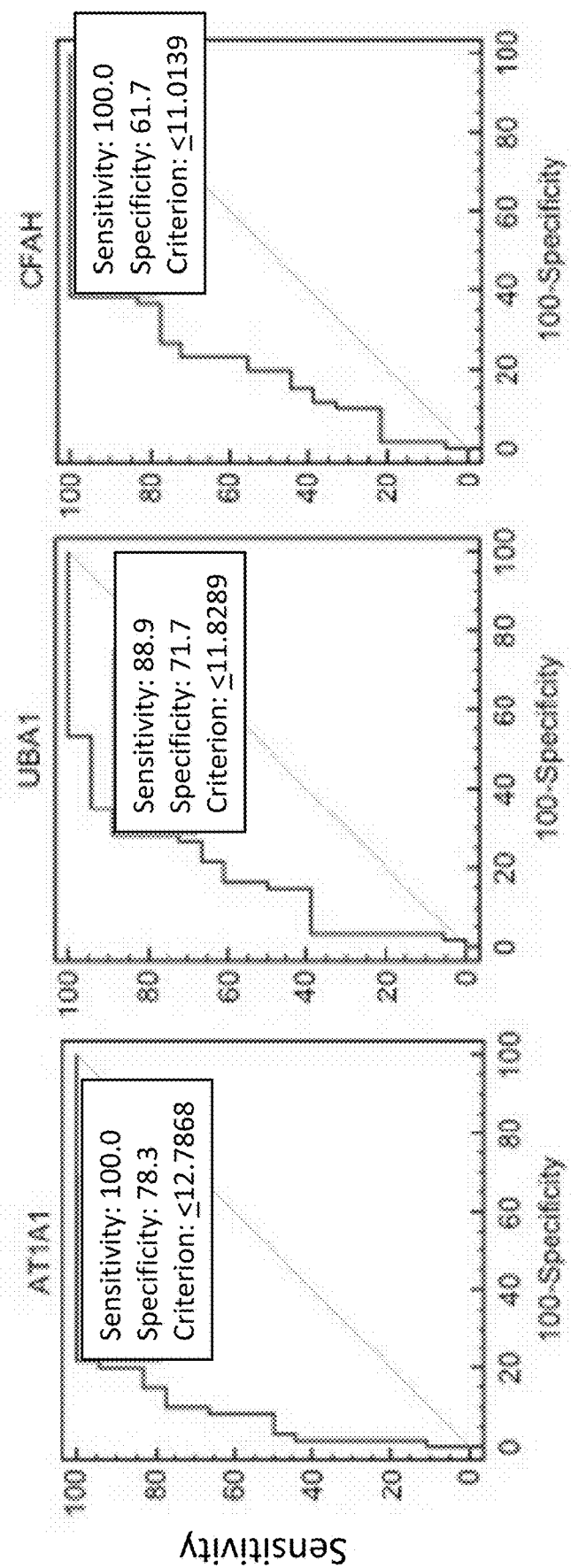
Figure 5H:
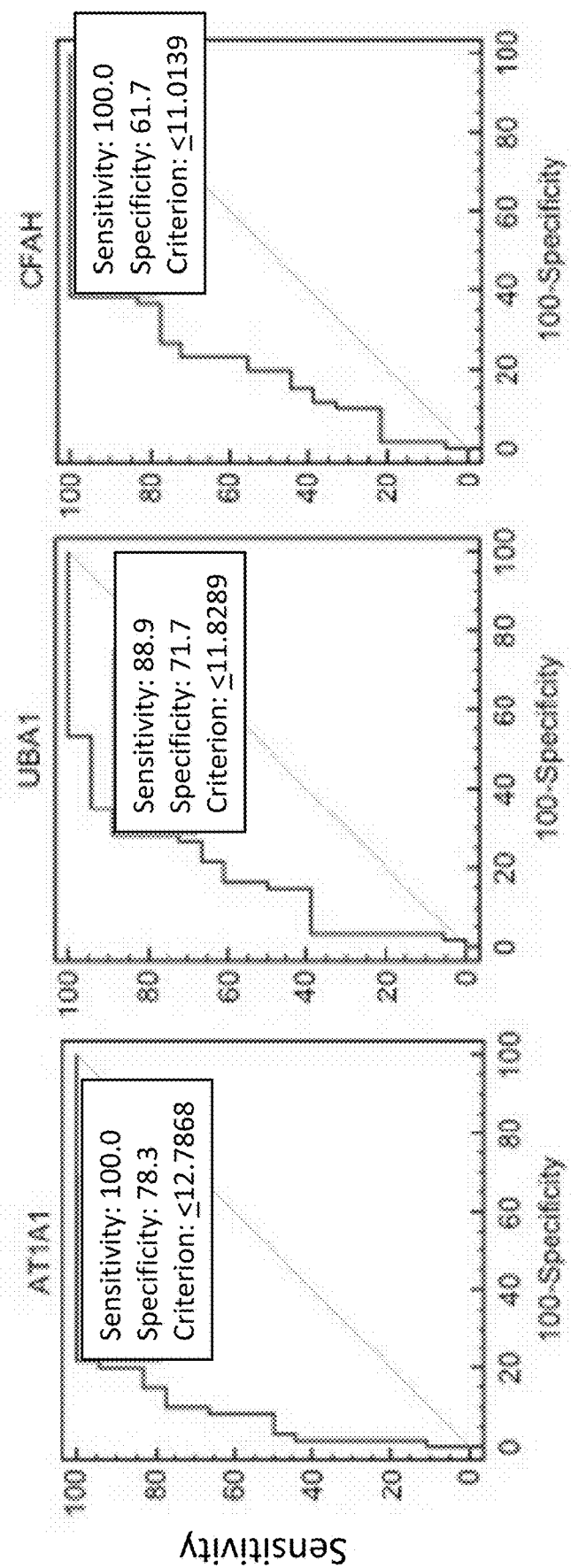
Figure 5I:
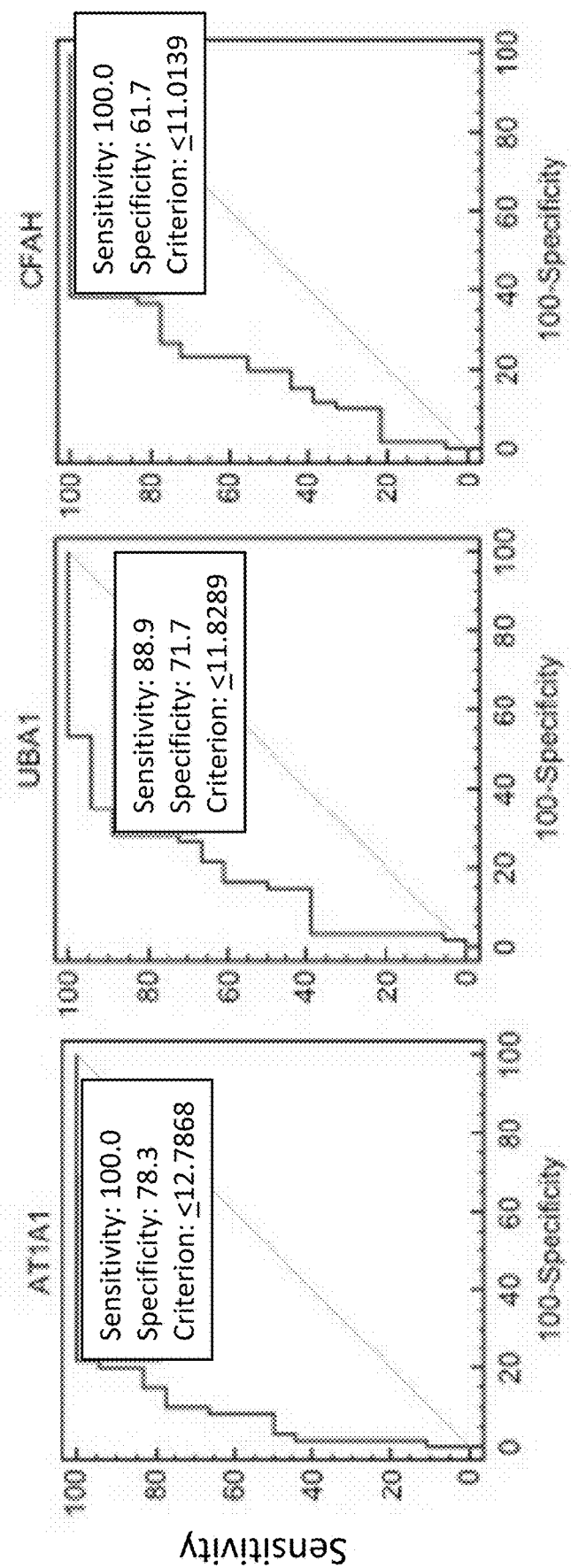

As only 68% of the data (1 standard deviation from the mean) appear to be normal (FIG. 3B), standard statistical methods cannot be used. Therefore, variance stabilisation and calibration (normalization) was performed prior to statistical analysis. Microarray intensity data were transformed using a VSN function in R that utilises affine-linear mappings and the generalised logarithm (base 2). Evaluation of the vsn-transformed microarray intensity data by q-q plot shows the data to be fairly normal as the central (middle) 95% of data lies along the straight line (FIG. 3D). Furthermore, the data no longer exhibits a variance-mean dependence (FIG. 3C). Therefore, parametric statistics can be used to assess significant differences in the data.

FIG. 4 shows the regulation pattern of the selected nine autoantibodies in early and late stage ovarian disease compared to health individuals and patients with benign gynaecological disease. Analysis of variance (ANOVA) was performed for each target antigen to determine whether the population means for the different cohorts (healthy, benign, early and late) were significantly different. Subsequent post-hoc analyses using Tukey's 'Honest Significant Difference' (HSD) test at a critical value of 0.05 was performed to determine which population means (cohorts) were significantly different from each other. Nine antigens were revealed to have the greatest significant difference between key cohorts as summarised in Table 4. As shown in FIG. 4, compared to healthy individuals and patients with benign gynaecological disease autoantibody levels to cancer antigens (A) ARP3, (B) SAHH and (C) ANXA1 are significantly regulated during both early and late stage cancer. Autoantibody levels to cancer antigens (D) SERPH, (E) ARAP1, (F) OTUB1 and (G) AT1A1 are significantly regulated during early stage cancer and somewhat regulated during late stage disease. Autoantibody levels to cancer antigens (H) UBA1 and (I) CFAH are significantly regulated during early stage cancer only.

TABLE 4

| Autoantibody | Early-Healthy | Early-Benign | Late-Healthy | Late-Benign |
|---|---|---|---|---|
| ARP3 | *** | *** | ** | ** |
| SAHH | *** | *** | * | *** |
| ANXA1 | *** | *** | ** | * |
| SERPH | *** | *** | 0.2347531 | * |
| ARAP1 | ** | ** | . | * |
| OTUB1 | *** | *** | * | 0.183457 |
| AT1A1 | *** | *** | * | 0.1147197 |
| UBA1 | ** | *** | 0.9999932 | 0.6047896 |
| CFAH | ** | ** | 0.896731 | 0.8498267 |

Note:

Significance p < 0.001 (***);

p < 0.01 (**);

p < 0.05 (*);

p < 0.1 (.)

Receiver operating characteristic curves of the nine autoantibody candidates were then assessed to determine their sensitivity and specificity for early ovarian disease. Relevant ROC curves are shown in FIG. 5. Anti-ARP3 appeared to be the superior candidate diagnostic autoantibody marker with the greatest area under the curve (AUC) of 0.94 as summarised in Table 5. At a sensitivity of 83% the top three candidate markers were able to identify 15/18 true positives, however, specificity varied at 98%, 97% and 92% for anti-ARP3, anti-ANXA1 and anti-SAHH, respectively. The remaining six autoantibody biomarkers also had a high AUC between 0.81 and 0.93 a shown in Table 6.

TABLE 5

| Auto-antibody | Sensitivity (%) | Specificity (%) | AUC | True Positives (/18) | True Negatives (/60) |
|---|---|---|---|---|---|
| ARP3 | 83.33 | 98.33 | 0.941 | 15 | 59 |
| ANXA1 | 83.33 | 96.67 | 0.891 | 15 | 58 |
| SAHH | 83.33 | 91.67 | 0.931 | 15 | 55 |

TABLE 6

| Autoantibody | AUC |
|---|---|
| AT1A1 | 0.925 |
| OTUB1 | 0.905 |
| SERPH | 0.898 |
| UBA1 | 0.83 |
| ARAP1 | 0.815 |
| CFAH | 0.811 |

Figure 6A:
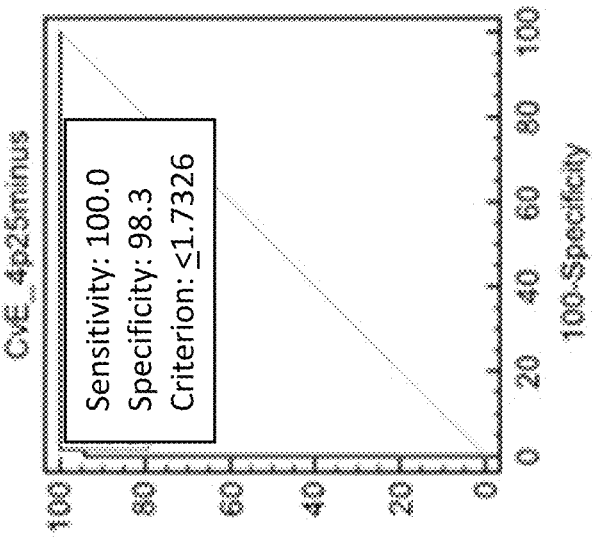
FIGS. 6A-6E— Receiver-operating characteristic (ROC) curves of combined autoantibody biomarker panels.
Figure 6B:
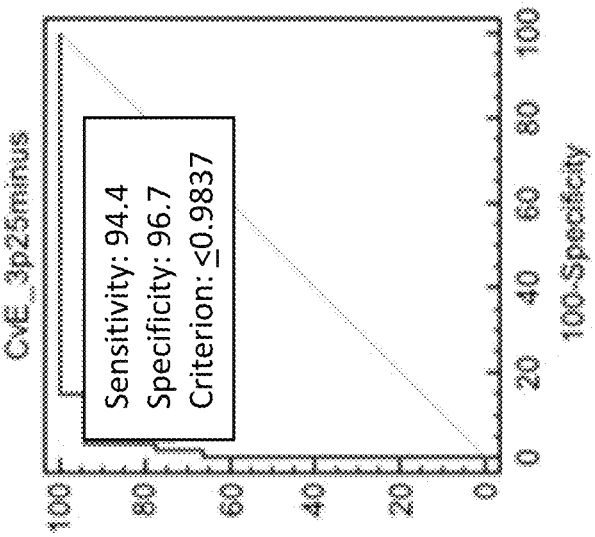
Figure 6C:
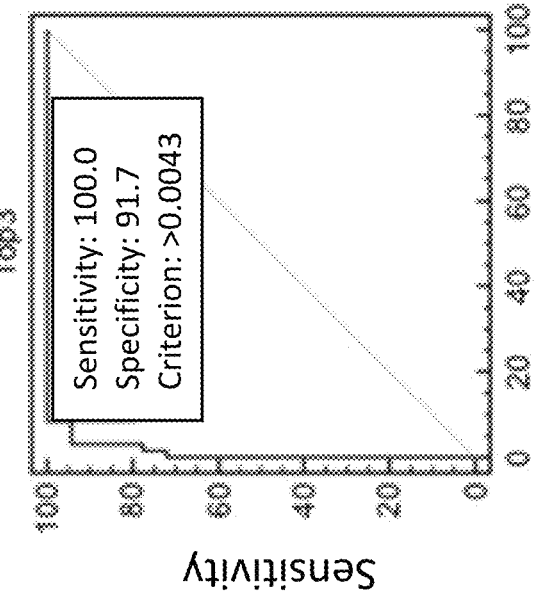

The top three autoantibody candidates were assessed as a biomarker panel with and without the tumour associated antigen CA125. The results are shown in FIG. 6. Linear discriminant analysis (LDA) was used on the normalised microarray intensity data to generate classifiers for anti-ARP3, anti-ANXA1 and anti-SAHH autoantibodies. Analysis of the complete data set (18 early stage, 30 healthy and 30 benign) using the generated classifiers resulted in a sensitivity and specificity of 100% and 91.7%, respectively (FIG. 6A). Alternatively, classifiers were generated with 25% of the data and the resultant parameters applied to classify the reaming 75% of the data. This exercise demonstrated the robustness of the biomarkers as a high sensitivity of 94.4% and specificity of 96.7% was maintained (FIG. 6B). Similarly, the top four autoantibody candidates (which included anti-ARP3, anti-ANXA1, anti-SAHH and anti-SERPH) were assessed by ROC, and showed the most promising results with respect to autoantibody combinations with a sensitivity of 100% and a specificity of 98.3% (FIG. 6C).

Figure 6E:
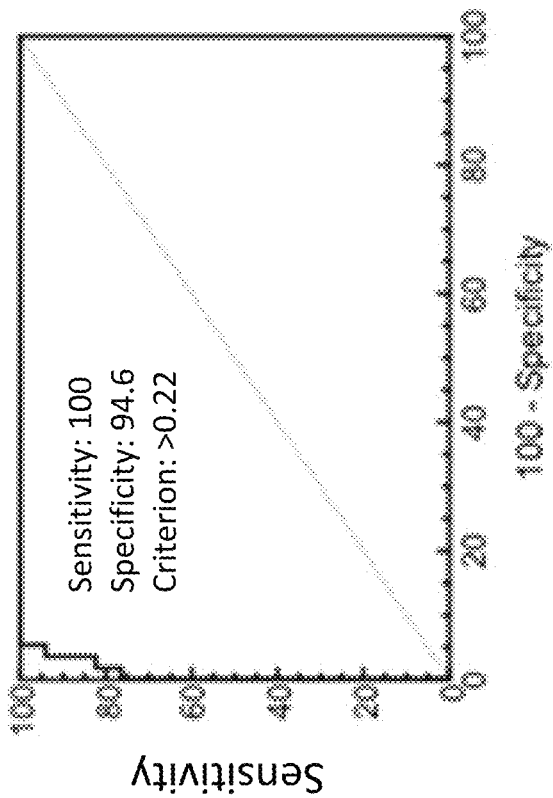
Figure 6D:
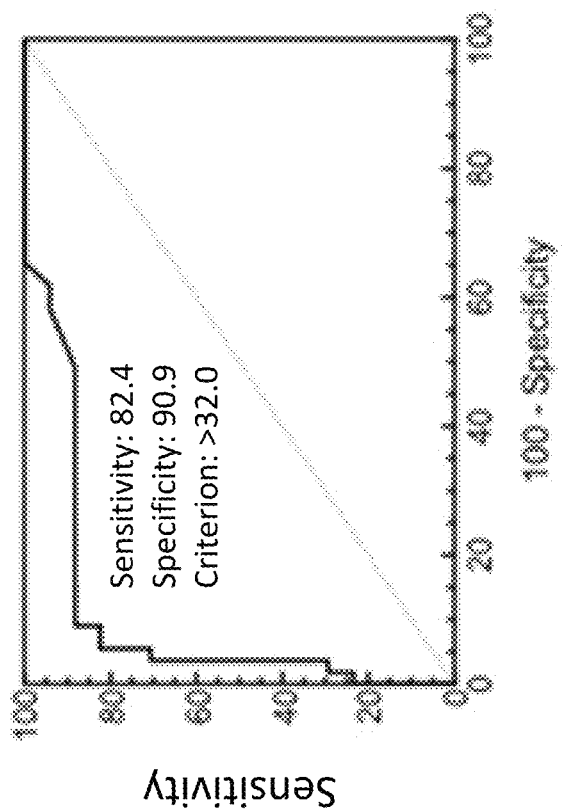

Furthermore, ROC analysis of early stage cancer samples (n=17) compared to controls (n=55) was performed using CA125 serum levels (FIG. 6D and Table 7). Interestingly, CA125 alone only had a sensitivity and specificity of 82.4% and 90.9%, respectively. When assessed in combination with our top three autoantibody biomarker panel (anti-ARP3, anti-ANXA1 and anti-SAHH) the sensitivity and specificity for early stage cancer detection was improved to 100% and 94%, respectively (FIG. 6E and Table 8). Accordingly, the aforementioned biomarker panels (anti-ARP3, anti-ANXA1 and anti-SAHH; anti-ARP3, anti-ANXA1, anti-SAHH and anti-SERPH; and CA125, anti-ARP3, anti-ANXA1 and anti-SAHH) offer an unexpected and significant advance with respect to sensitivity and specificity over current markers for ovarian cancer, including early stage ovarian cancer.

TABLE 7

| Criterion (U/mL) | Sensitivity (%) | Specificity (%) | AUC | True Positives (/17) | True Negatives (/55) |
|---|---|---|---|---|---|
| >31.0 | 82.4 | 90.9 | 0.90 | 14 | 50 |

TABLE 8

| Biomarker combination | AUC |
|---|---|
| CA125 | 0.9032 |
| CA125 + ARP3 | 0.9519 |
| CA125 + ANXA1 | 0.9016 |
| CA125 + SAHH | 0.9679 |
| CA125 + ARP3 + ANXA1 | 0.9872 |
| CA125 + ARP3 + SAHH | 0.9701 |
| CA125 + ANXA1 + SAHH | 0.9850 |
| CA125 + ARP3 + ANXA1 + SAHH | 0.9914 |

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The invention claimed is:

1. A method of detecting and treating early stage ovarian cancer in a subject, the method comprising:
    detecting a decrease in autoantibodies to ANXA1 in a sample obtained from the subject compared to a reference level of a normal subject; and
    treating the subject with conventional ovarian cancer therapy.

2. The method according to claim 1, wherein the sample is selected from any one or more of the group consisting of serum, whole blood, blood plasma, saliva, buccal swab, cervical pap smears, stool, urine, bladder washing, uterine washing, sputum, lymphatic fluid, cerebrospinal fluid, and a tissue sample from one or both ovaries or metastatic tumour tissue of the subject.

3. The method according to claim 1, wherein the decrease in autoantibodies to ANXA1 is detected by an agent that binds to, or interacts with, autoantibodies to ANXA1.

4. The method according to claim 3, wherein the agent is an antigen from which the ANXA1 autoantibodies were derived, or is an antibody specific for the ANXA1 autoantibodies.

5. The method according to claim 3, wherein the agent is detectably labelled.

6. The method according to claim 1, further comprising detecting one or more of a decrease in autoantibodies to SERPH, a decrease in autoantibodies to ARAP1, a decrease in autoantibodies to OTUB1, a decrease in autoantibodies to ATP1A1, a decrease in autoantibodies to UBA1, and an increase in autoantibodies to CFAH.

7. The method of claim 6, further comprising detecting the presence of tumour associated antigen CA125.

8. The method according to claim 1, wherein the early stage ovarian cancer is stage I carcinoma.

9. The method according to claim 1, wherein the conventional ovarian cancer therapy comprises chemotherapy or radiotherapy.

10. A method of detecting early stage ovarian cancer in a subject, the method comprising detecting a decrease in autoantibodies to ANXA1 in a sample obtained from the subject compared to a reference level of a normal subject, thereby detecting early stage ovarian cancer in the subject, wherein the method further comprises treating the subject with conventional ovarian cancer therapy.

11. The method according to claim 10, wherein the sample is selected from any one or more of the group consisting of serum, whole blood, blood plasma, saliva, buccal swab, cervical pap smears, stool, urine, bladder washing, uterine washing, sputum, lymphatic fluid, cerebrospinal fluid, and a tissue sample from one or both ovaries or metastatic tumour tissue of the subject.

12. The method according to claim 10, wherein the early stage ovarian cancer is stage I carcinoma.

13. The method according to claim 10, wherein the conventional ovarian cancer therapy comprises chemotherapy or radiotherapy.

14. A method comprising:
detecting a decrease in autoantibodies to ANXA1 in a serum sample obtained from a subject compared to a reference level of a normal subject and treating the subject with conventional ovarian cancer therapy.

15. The method according to claim 14, wherein the decrease in autoantibodies to ANXA1 is detected by an agent that binds to, or interacts with, autoantibodies to ANXA1.

16. The method according to claim 15, wherein the agent is an antigen from which the ANXA1 autoantibodies were derived, or is an antibody specific for the ANXA1 autoantibodies.

17. The method according to claim 14, wherein the subject has at least one risk factor for ovarian cancer.

18. The method according to claim 17, wherein the subject carries a BRCA1 or BRCA2 mutation.

19. The method according to claim 14, further comprising detecting one or more of a decrease in autoantibodies to SERPH, a decrease in autoantibodies to ARAP1, a decrease in autoantibodies to OTUB1, a decrease in autoantibodies to ATP1A1, a decrease in autoantibodies to UBA1, and an increase in autoantibodies to CFAH.

20. The method according to claim 14, wherein the conventional ovarian cancer therapy comprises chemotherapy or radiotherapy.

* * * * *